United States Patent
Chase et al.

(10) Patent No.: US 9,943,508 B2
(45) Date of Patent: *Apr. 17, 2018

(54) METHOD AND COMPOSITION FOR TREATING ALZHEIMER-TYPE DEMENTIA

(71) Applicant: Chase Pharmaceuticals Corporation, Parsippany, NJ (US)

(72) Inventors: Thomas N. Chase, Washington, DC (US); Kathleen E. Clarence-Smith, Washington, DC (US)

(73) Assignee: Chase Pharmaceuticals Corporation, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/651,324

(22) Filed: Jul. 17, 2017

(65) Prior Publication Data

US 2017/0312259 A1 Nov. 2, 2017

Related U.S. Application Data

(63) Continuation of application No. 15/010,452, filed on Jan. 29, 2016, now Pat. No. 9,744,161, which is a
(Continued)

(51) Int. Cl.

| | | |
|---|---|---|
| *A01N 43/42* | (2006.01) | |
| *A01N 43/36* | (2006.01) | |
| *A61K 31/44* | (2006.01) | |
| *A61K 31/439* | (2006.01) | |
| *A61K 31/352* | (2006.01) | |
| *A61K 31/166* | (2006.01) | |
| *A61K 9/00* | (2006.01) | |
| *A61K 9/48* | (2006.01) | |
| *A61K 9/20* | (2006.01) | |
| *A61K 31/4965* | (2006.01) | |
| *A61K 31/27* | (2006.01) | |
| *A61K 31/353* | (2006.01) | |
| *A61K 31/4178* | (2006.01) | |
| *A61K 31/4184* | (2006.01) | |
| *A61K 31/46* | (2006.01) | |
| *A61K 31/473* | (2006.01) | |
| *A61K 31/496* | (2006.01) | |
| *A61K 31/5377* | (2006.01) | |
| *A61K 31/55* | (2006.01) | |
| *A61K 45/06* | (2006.01) | |

(Continued)

(52) U.S. Cl.
CPC .......... *A61K 31/439* (2013.01); *A61K 9/0014* (2013.01); *A61K 9/0053* (2013.01); *A61K 9/0056* (2013.01); *A61K 9/205* (2013.01); *A61K 9/2018* (2013.01); *A61K 9/2054* (2013.01); *A61K 9/2059* (2013.01); *A61K 9/4808* (2013.01); *A61K 31/166* (2013.01); *A61K 31/27* (2013.01); *A61K 31/352* (2013.01); *A61K 31/353* (2013.01); *A61K 31/407* (2013.01); *A61K 31/4178* (2013.01); *A61K 31/4184* (2013.01); *A61K 31/445* (2013.01); *A61K 31/454* (2013.01); *A61K 31/46* (2013.01); *A61K 31/473* (2013.01); *A61K 31/496* (2013.01); *A61K 31/4965* (2013.01); *A61K 31/5377* (2013.01); *A61K 31/55* (2013.01); *A61K 45/06* (2013.01)

(58) Field of Classification Search
None
See application file for complete search history.

(56) References Cited

U.S. PATENT DOCUMENTS

| | | |
|---|---|---|
| 5,576,317 A | 11/1996 | Gonsalves |
| 5,854,270 A | 12/1998 | Gambhir |

(Continued)

FOREIGN PATENT DOCUMENTS

| | | |
|---|---|---|
| EP | 0236684 | 2/1987 |
| EP | 0976404 | 2/2000 |
| JP | 62215527 | 9/1967 |
| JP | 2000143541 | 5/2000 |
| JP | 2011518776 | 6/2011 |
| WO | 2004069246 | 8/2004 |
| WO | 2005073198 | 8/2005 |
| WO | 2007517905 | 7/2007 |
| WO | 2008033299 | 3/2008 |
| WO | 2009120277 | 10/2009 |

OTHER PUBLICATIONS

Doody et al., Safety and Tolerability of Donepezil at Doses up to 20 mg/day, Drugs & Aging, Feb. 2008, vol. 25, Issue 2, pp. 163-174.*

(Continued)

*Primary Examiner* — Svetlana M Ivanova
(74) *Attorney, Agent, or Firm* — Sughrue Mion, PLLC

(57) ABSTRACT

There is described a method for increasing the maximal tolerated dose and thus the efficacy of an acetyl choline esterase inhibitor (AChEI) in a patient suffering from an Alzheimer type dementia by decreasing concomitant adverse effects by administration of said AChEI in combination with a non-anticholinergic antiemetic agent, whereby an enhanced acetyl choline esterase inhibition in the CNS of said patient is achieved and alleviation of the symptoms of Alzheimer type dementia in said patient is thereby improved to a greater extent. The use of a non-anticholinergic antiemetic agent for the preparation of a pharmaceutical composition for the treatment of Alzheimer type dementia in combination with an acetyl choline esterase inhibitor (AChEI) and pharmaceutical compositions comprising (a) a $5HT_3$ receptor antagonist, a dopamine antagonist, a H1-receptor antagonist, a cannabinoid agonist, aprepitant or casopitant as an antiemetic agent and (b) an acetylcholine esterase inhibitor are also described.

23 Claims, No Drawings

Related U.S. Application Data continuation of application No. 14/489,827, filed on Sep. 18, 2014, now Pat. No. 9,278,092, which is a continuation of application No. 12/880,395, filed on Sep. 13, 2010, now Pat. No. 8,877,768.

(60) Provisional application No. 61/272,382, filed on Sep. 18, 2009.

(51) Int. Cl.
  A61K 31/445 (2006.01)
  A61K 31/454 (2006.01)
  A61K 31/407 (2006.01)

(56) References Cited

U.S. PATENT DOCUMENTS

| | | | |
|---|---|---|---|
| 8,877,768 B2* | 11/2014 | Chase | A61K 31/166 514/278 |
| 9,192,591 B2 | 11/2015 | Chase | |
| 9,278,092 B2* | 3/2016 | Chase | A61K 31/166 |
| 9,744,161 B2* | 8/2017 | Chase | A61K 31/439 |
| 2005/0010259 A1 | 1/2005 | Gerber | |
| 2005/0065176 A1 | 3/2005 | Field et al. | |
| 2006/0293356 A1 | 12/2006 | Aberg | |
| 2007/0053982 A1 | 3/2007 | Ogorka et al. | |
| 2007/0249869 A1 | 10/2007 | Sellstedt et al. | |
| 2007/0259933 A1 | 11/2007 | Virsik et al. | |
| 2008/0114014 A1 | 5/2008 | Rich | |
| 2011/0021503 A1 | 1/2011 | Chase et al. | |
| 2011/0071135 A1 | 3/2011 | Chase et al. | |
| 2011/0201597 A1 | 8/2011 | Chase et al. | |

OTHER PUBLICATIONS

Aricept(R) (Donepezil Hydrochloride Tablets) NDA 20-690/ S-026 (no date) ("Donepezil drug label", of record).*
"Guidance for Industry: Estimating the Maximum Safe Starting Dose in Initial Clinical Trials for Therapeutics in Adult Healthy Volunteers", Pharmacology and Toxicology, pp. 1-27 (2005).
Aricept® (Donepezil Hydrocholride Tablets) NDA 20-690/S-026, Packaging, Eisai Co., Ltd., pp. 3-30.
Bennett et al., "Cognitive Deficits in Rats after Forebrain Cholinergic Depletion are reversed by a novel NO Mimetic Nitrate Ester", Neuropsychopharmacology, 32:505-513 (2007).
Schultz-Lampel, "Blasendysfunktion bei Demenz und M. Alzheimer [Bladder disorders in patients with dementia]", Urologe A., 42(12):1579-1587 (2003), Abstract XP002489800.
Diez-Ariza et al., "Flumazenil and tacrine increase the effectiveness of ondansetron on scopolamine-induced impairment of spatial learning in rats", Psychopharmacology, 169:35-41 (2003).
Siegler et al., "Treatment of urinary incontinence with anticholinergics in patients taking cholinesterase inhibitors for dementia", Clinical Pharmacology and Therapeutics, 75(5):484-488 (2004), Abstract XP009102926.
Extended Search Report issued in corresponding European Patent Application No. 10817543 dated Jan. 4, 2013.
Fu et al., "Propantheline Attenuates the Peripheral Side Effects of Donepezil without Affecting Its Antiamnestic Properties in Cerebral Ischemic Mice", Journal of Health Science, 54(4):409-415 (2008).
Forette et al., "A phase II study in patients with Alzheimer's disease to assess the preliminary efficacy and maximum tolerated dose of rivastigmine (Exelon (R))", European Journal of Neurology, 6:423-429 (1999).
Glycopyrrolate Tablet, Daily Med (Current Medical Information), Westward Pharmaceutical Corporation, Human Prescription Drug Label, retrieved at http://dailymed.nlm.nih.gov/dailymed/drugInfo.cfm?id=65407, pp. 1-5 (Jun. 5, 2012).
Gottfries, "Alzheimer's disease and senile dementia: Biochemical characteristics and aspects of treatment", Psychopharmacology, 86:245-252 (1985).
Cappon et al., "Tolterodine does not affect memory assessed by passive-avoidance response test in mice", European Journal of Pharmacology, 579:225-228 (2008), Abstract XP002489794.
Madersbacher, "Orale Anticholinergika bei uberaktiver Blase [Oral anticholinergics in overactive bladder]", Der Urologe. Ausg. A, 45(7):830-834 (2006).
Honma et al, "Current status and prospects of therapeutic agents for Alzheimer—from mechanisms thereof", Japanese Journal of Geriatric Psychiatry, 17(1):23-32 (2006).
Ikeda et al., Overactive Bladder Induced by Higher Dose of Donepezil Hydrochloride in a Patient with Senile Dementia of Alzheimer Type, Neurological Therapeutics, 25:609-612 (2008).
Jann et al., "Clinical Pharmacokinetics and Pharmacodynamics of Cholinestrase Inhibitors", Clinical Pharmacokinet., 41(10):719-739 (2002).
Jhee et al., "Centrally Acting Antiemetics Mitigate Nausea and Vomiting in Patients With Alzheimer's Disease Who Receive Rivastigmine", Clinical Neuropharmacology, 25(2):122-123 (2002).
Kirby et al., Effects of anticholinestrerase drugs tacrine and E2020, the 5-HT3 antagonist, and the H3 antagonist thioperamide, in models of cognition and cholinergic function, Behavioural Pharmacology, 7:513-525 (1996).
Kobayashi, "Treatment of dementia in United States, Guidelines for case and problems", Japanese Journal of Geriatric Psychiatry, 20(4):399-406 (2009).
Letters to the Editor, American J. Psychiatry, pp. 156-161 (Jan. 1999).
Doody et al., Safety and tolerability of donepezil at doses up to 20 mg/day: results from a pilot study in patients with Alzheimer's disease, Drugs & Aging, 25(2):163-174 (2008).
Takeda et al., "Effects of Anti-Cholinergics on Cognitive Functions, Urinary Symptoms, Urinary Functions, and Impacts of Caregiver in Elderly Dementia Patients with Urinary Incontinence—A Prospective Randomized Study", $33^{rd}$ Annual Meet. Int. Continence Soc., Florence, Abstract 166 (XP009102822) (Oct. 5-9, 2003).
Magari et al., "Therapeutic Effects of Solifenacin Succinate on OAB: QOL Assessments using VAS in Cases with Pretreatment", The Japanese Journal of Urology, 99(2):323 (2008).
Martin et al., "Office evaluation of dementia: How to arrive at a clear diagnosis and choose appropriate therapy", Dementia, 84(3):176-187 (1988).
Suzuki et al., "Effect of antimuscarinic drugs used for overactive bladder on learning in a rat passive avoidance response test", European Journal of Pharmacology, 557:154-158 (2007).
Cutler et al., "Antiemetic Therapy for Alzheimer's Patients Receiving the Cholinesterase Inhibitor SDZ ENA 713", Clinical Pharmacology & Therapeutics, 63(2):88 (PII-62) (1998).
Notification of Reasons for Rejection for Japanese Application No. 2016-078787 dated Apr. 4, 2017.
Notification of Reasons for Rejection for Japanese Application No. 2012-529733 dated Jul. 17, 2014.
Communication for European Application No. 17150365.9 dated May 15, 2017, with European Search Report (dated May 9, 2017).
Notification of Reasons for Rejection for Japanese Application No. 2012-529733 dated Apr. 12, 2016.
International Preliminary Report on Patentability in PCT/US2010/002475 dated Mar. 29, 2012.
Novartis Pharmaceutical Corporation: "Exelon", 2006, retrieved from: http://www.pharma.us.novartis.com/cs/www.pharma.us.novartis.com/product/pi/pdf/exelon.pdf on Dec. 13, 2012.
Faber et al., "Enhancing the Tolerability of Tacrine with Propantheline", Am. J. Psychiatry, 156(1):156 (1999), PubMed: 9892315, Abstract XP002631460.
Scheife et al., "Central Nervous System Safety of Anticholinergic Drugs for the Treatment of Overactive Bladder in the Elderly", Clinical Therapeutics, 2(2):144-153 (2005), Abstract XP004874590.
Ropper, "A rational approach to dementia", CMA Journal, 121:1175-1190 (1979).
Sakakibara et al., "Care of OAB in elderly patients with dementia: therapy using a combination of donepezil and propiverine", The Japanese Journal of Urology, 99(2):323 (2008).

(56) References Cited

OTHER PUBLICATIONS

Scarzella, "Domperidone is effective in teh prevention of rivastigmine-related gastrointestinal disturbances", Functional Neurology, 22(2)101-104 (2007).

Anghelescu et al., "Acetylcholinesterasehemmer bei Demenz Lohnt die antidementive Therapie", MMW Fortschritte der Medizin, 149(2):76-78 (2007).

Zhang et al., "Peripheral cholinoceptor antagonist anisodamine counteracts cholinergic adverse effects and facilitates cognitive amelioration of rivastigmine", J. Neural. Transm., 116(12):1643-1649 (2009).

Wilcock et al., "Efficacy and safety of galantamine in patients with mild to moderate Alzheimer's disease: multicentre fandomised controlled trial", BJM, 321:1145, doi:http//dx.doi.org/10.1136/bjm. 322.7274.1445 (2000).

ARICEPT®, Center for Drug Evaluation and Research, Clinical Pharmacology Review, Clinical Pharmacology and Biopharmaceutics Review(s), NDA 22-568, Eisai Medical Research Inc., 12 pages (Sep. 24, 2009).

Bejar et al., "Effect of Rivastigmine on Scopolamine-Induced Memory Impairment in Rats", European Journal of Pharmacology, 383:231-240 (1999).

Maugh II, "High dose of Alzheimer's drug Aricept should be banned, Public Citizen says", Los Angeles Times (May 18, 2011).

Van Dam et al., " Symptomatic effect of donepezil, rivastigmine, galantamine and memantine on cognitive deficits in the APP23 model", Psychopharmacology, 180:177-190 (2005).

\* cited by examiner

METHOD AND COMPOSITION FOR TREATING ALZHEIMER-TYPE DEMENTIA

CROSS-REFERENCE TO RELATED APPLICATIONS

This application is a Continuation of Ser. No. 15/010,452, filed Jan. 29, 2016 (now allowed); which is a Continuation of Ser. No. 14/489,827, filed Sep. 18, 2014 (now U.S. Pat. No. 9,278,092); which is a Continuation of U.S. application Ser. No. 12/880,395, filed Sep. 13, 2010 (now U.S. Pat. No. 8,877,768), which claims the benefit of provisional application Ser. No. 61/272,382 filed Sep. 18, 2009, the entire content of each of which is hereby incorporated by reference in this application.

FIELD OF THE INVENTION

This invention concerns a method for enhancing the maximal efficacy and maximal tolerated dose of an acetyl choline esterase inhibitor in a patient suffering from dementia of the Alzheimer type by combining said acetyl choline esterase inhibitor with an antiemetic agent, or the use of an antiemetic agent substantially devoid of central anticholinergic activity for the preparation of pharmaceutical compositions for the treatment of Alzheimer type dementias in combination with an acetyl choline esterase inhibitor (AChEI). The invention also concerns pharmaceutical compositions comprising an antiemetic agent, in particular a serotonin $5HT_3$ receptor antagonist compound in association with an acetylcholine esterase inhibitor to allow increasing and prolonging efficacy and decreasing toxicity of these conventional cholinomimetic treatments such as treatments for dementias in diseases of the Alzheimer type.

DEFINTIONS

"AChEI(s)": Acetyl Choline Esterase Inhibitor(s).
"CNS": Central Nervous System.
"PNS": Peripheral Nervous System.
"IR": Immediate Release of the active ingredient from a composition.
"ER": Extended Release of the active ingredient from a composition.
"Non-anticholinergic" refers to antiemetic medications not primarily regarded as anticholinergic agents; they are entirely devoid of anticholinergic activity or have an extremely low ability to prevent acetylcholine from acting at its cholinergic receptor sites.

BACKGROUND OF THE INVENTION

Dementias of the Alzheimer type include, but are not limited to Alzheimer's disease, Parkinson's disease dementia, and related maladies in humans involving cognitive and behavioral dysfunction such as Lewy body dementia. Most are chronic neurodegenerative disorders of the human central nervous system (CNS) characterized by progressive cognitive impairment, a variety of neurobehavioral and/or neuropsychiatric disturbances, and restrictions in activities of daily living.

Alzheimer's disease is the most common form of dementia. Prevalence studies indicated that in 2000 there were about 25 million persons with Alzheimer's disease worldwide and this number is expected to increase to 114 million by 2050 unless an effective preventive or neuroprotective therapy emerges. Onset usually occurs in those over age 65. Clinical signs include progressive cognitive loss and other associated neurobehavioral disabilities together with a declining capability of performing the activities of daily living.

The basic cause of sporadic Alzheimer's disease is not known, probably because the disease is heterogeneous and involves age-related changes together with a complex interaction of genetic and environmental risk factors. Current hypotheses advanced to explain the pathophysiology of Alzheimer's disease center on the putative deleterious effects of the two misfolded and aggregated proteins, extracellular beta amyloid and intracellular tau. Presumably, as a consequence of the selective neurodegenerative process, the synthesis of the neurotransmitter acetylcholine declines. This reduction undoubtedly interferes with normal synaptic transmission in brain. Drugs that act to correct the acetylcholine deficiency thus constitute the mainstay of current therapy.

Dementias of the Alzheimer type also include cognitive impairments associated with Parkinson's disease. One example is Parkinson's disease dementia, also a chronic progressive CNS degenerative disorder with relatively late life onset. Parkinson's disease itself primarily affects motor function. But secondary symptoms include cognitive deterioration, especially deficits in executive function.

Another dementia of the Alzheimer type that is commonly linked to Parkinson's disease is known as dementia with Lewy bodies or Lewy body dementia. Although Lewy body dementia is now generally regarded as a separate disease, differentiation from Alzheimer's disease and from Parkinson's disease dementia may be clinically challenging. Lewy body dementia thus tends to be under-diagnosed or misdiagnosed as Alzheimer's disease or Parkinson's disease dementia. The clinical presentation of Lewy body dementia is typically one of cortical and subcortical cognitive impairment, with visuospatial and executive dysfunction more pronounced than in Alzheimer's disease. Core clinical features of Lewy body dementia, in addition to parkinsonism, are cognitive decline plus fluctuations in attention and recurrent visual hallucinations.

Both Parkinson's disease dementia and Lewy body dementia are characterized neuropathologically by the presence of cortical Lewy body pathology and synuclein protein deposition. Genetic factors appear to play a role in pathogenesis. Not surprisingly, the pathology of Parkinson's disease dementia and Lewy body dementia is heterogeneous and overlapping, often intermixed with changes of the Alzheimer and vascular types. A reduction in brain acetylcholine-mediated neurotransmission has been linked to the primary clinical abnormalities found in both these disorders and drugs acting to stimulate cholinergic transmission now constitute the main approach to therapy.

In addition to the aforementioned disorders, the off label administration of drugs that augment CNS cholinergic transmission for various other cognitive disorders is widespread. Some of this use involves cognitive disorders for which relatively little clear evidence of cholinergic dysfunction currently exists. Nevertheless, an increasing number of clinical studies now support a rational extension of AChEI treatment to various additional disorders of cognitive function, including but not limited to, vascular dementia, Down syndrome, traumatic brain injury and mild cognitive impairment.

As noted above, reduced levels of neurotransmitters including acetylcholine have been reported in dementias of the Alzheimer type and related disorders. In particular, a deficit in acetylcholine-mediated transmission is thought to contribute to the cognitive and certain of the neurobehavioral abnormalities associated with these disorders. Accordingly, drugs known to augment cholinergic transmission in the CNS are widely used in therapy.

AChEIs are now part of the standard care for patients suffering from a dementia of the Alzheimer type and are widely used off label for various other chronic progressive disorders of cognitive function. AChEIs have the enhancement of acetylcholine-mediated neurotransmission as a general mechanism of action. All act in the human CNS to increase and prolong the availability of acetylcholine by inhibiting its degradatory enzyme acetylcholinesterase. Four AChEIs have been approved by the U.S. FDA for the treatment of Alzheimer's disease and for Parkinson's disease dementia: tacrine, donepezil [Aricept®], rivastigmine [Exelon®] and galantamine [Razadyne®]. AChEIs are available in various formulations including immediate release forms such as tablets, capsules and solutions as well as rapid dissolving and extended release forms for oral administration as well as those for parenteral (e.g. transdermal) administration.

Other AChEIs, in particular tacrine analogs, such as ipidacrine; phenserine and their analogs; icopezil; and zanapezil are under evaluation.

Augmentation of cholinergic transmission in the CNS by currently available AChEIs confers therapeutic benefit to patients with Alzheimer type dementias. Therapeutic efficacy can be measured by the degree of improvement in cognitive dysfunction and other neurobehavioral abnormalities associated with these disorders using standardized scales.

Unfortunately, however, none of the currently available cholinomimetic or medications offer more than modest clinical benefit for some patients suffering from any of the aforementioned dementing disorders, even when these medications are administered at their maximum safe and tolerated doses. This is the first problem limiting the success of current AChEI therapy of Alzheimer type dementias.

Carefully conducted clinical trials of donepezil (Rogers et al., Neurology 1998, 50, 136-45; Winblad et al. Neurology. 2001 Aug. 14; 57(3):489-95), rivastigmine (Rösler et al., Brit. Med. J. 1999, 318, 633-38; Farlow et al. Eur. Neurol., 2000, 44, 236-41) and galantamine (Raskind et al., Neurology, 2000, 54, 2261-68; Tariot et al., Neurology, 2000, 54, 2269-76) in patients with dementias of the Alzheimer type demonstrated small, but statistically significant, benefits on cognitive and global measures relevant to dementia. The magnitude of the effect in pivotal clinical trials was on the order of a 2.8 point improvement on the 70-point cognitive subscale of the Alzheimer's Disease Assessment Scale (ADAS-Cog), or 1-1.5 point improvement on the 30-point Mini-Mental Status Examination (MMSE) compared to placebo over six months. Differences in global measures assessed by the 7-point Clinician Interview-Based Impression of Change scale (CIBIC) were on the order of 0.3-0.5 points in patients receiving an AChEI compared to those receiving placebo. Efficacy was similar for the three commonly used AChEIs. AChEIs also appear to have a beneficial effect on the behavioral and neuropsychiatric symptoms in patients with Alzheimer type dementias.

A second problem limiting the success of current AChEI therapy of Alzheimer type dementias is that, even at recommended amounts, all these drugs produce dose limiting adverse reactions. These side effects commonly include, for the aforementioned AChEIs tacrine, donepezil, rivastigmine and galantamine: anorexia, nausea, vomiting, diarrhea, abdominal pain and weight loss (Physicians Desk Reference 2008, Thomson PDR, Montvale, N.J.).

The most frequently reported adverse effects of rivastigmine, for example, are gastrointestinal, especially nausea. About half of patients who take this drug in the recommended therapeutic oral dose range of 6-12 mg/day become nauseated and about one-third vomit at least once. Vomiting was severe in 2% of rivastigmine-treated patients and was mild or moderate in 14%. Five percent of patients discontinued rivastigmine because of vomiting, compared to less than 1% on placebo. A loss of appetite was reported by 17% of patients, and weight declined in 25% during rivastigmine therapy (averaging 7 to 10 pounds). Presumably, the drug-induced anorexia, nausea and vomiting contribute to the observed weight loss. These untoward gastrointestinal effects, as well as others occurring with AChEI treatment, make it difficult to increase rivastigmine dosage above 6 mg daily in most patients.

Adverse events significantly reduce the safety and tolerability of AChEI therapy. Attempts to limit them in clinical practice now rely on initiating treatment with a low dose and then escalating the dose slowly. Nevertheless, in current clinical practice, AChEI dosage is guided mainly by side effects and not by therapeutic effects in contrast to most drugs used in the treatment of neuropsychiatric disease. The administration of higher doses than recommended doses tends to increase the frequency and severity of these side effects as well as introduce additional kinds of adverse reactions. These include those generally found with high dose administration of cholinomimetics. In view of the frequency and potential severity of these high dose adverse effects, maximum recommended oral doses of AChEIs are rarely intentionally exceeded in clinical practice.

It is reported that recommended maximal dose levels of these drugs typically achieve only about 45% acetyl cholinesterase inhibition in the CNS of Alzheimer disease patients (Brannan S et al. ACNP 46$^{th}$ Annual Meeting, Program No. 4. Boca Raton Fla., Dec. 10, 2007—"Brannan 2007") and that inhibition of acetyl cholinesterase activity and cognitive improvement are significantly correlated (Giacobini et al. J Neural Transm. 2002 July; 109(7-8):1053-65) and that, ordinarily, a higher degree of enzyme blockade must be attained for maximum functional effect (Jann et al., Clin Pharmacokinet. 2002; 41(10):719-39—"Jann 2002").

On the other hand, doubling the dose of rivastigmine, which became clinically practical when AChEI administration by immediate release tablets was replaced by skin patches, which diminished side effects by blunting peak blood levels, significantly increased the amount of cognitive improvement in patients with Alzheimer's disease without increasing side effects.

By virtue of being dose limiting, these adverse effects also constrain the efficacy of AChEI therapy. Studies in animal models of human cognitive dysfunction indicate a direct dose-response relation between the amount of acetyl choline esterase inhibition and the degree of cognitive improvement (Bennett B M et al., Neuropsychopharmacology. 2007 March; 32(3):505-13). Similar conclusions have been drawn regarding AChEI effects on cognitive and behavioral symptoms in human patients with Alzheimer's disease (Jann 2002; Winblad B, Cummings J, Andreasen N, Grossberg G, Onofrj M, Sadowsky C, Zechner S, Nagel J, Lane R. Int J Geriatr Psychiatry. 2007 May; 22(5):456-67).

The precise causes of the vomiting and related gastrointestinal symptoms induced by AChEI therapy are not known. Presumably, they reflect the cholinergic receptor hyperstimulation attending AChEI administration. Vomiting is coordinated in a center located at the base of the brain. The vomiting center communicates with the nearby chemoreceptor trigger zone, whose stimulation can lead to such complaints of gastrointestinal distress as anorexia, nausea and vomiting. The chemoreceptor trigger zone, which contains numerous serotonin 5-HT3 and dopamine D2 receptors as well as those for acetylcholine, opioids and substance P, lies outside the blood-brain barrier. Systemically administered antiemetics acting at these or related transmitter receptor sites can thus inhibit vomiting even if unable to enter the CNS.

PRIOR ART

A benefit of alleviating the side effects of an AChEI was described in a report of four patients in whom the treatment of Alzheimer's disease with the AChEI tacrine was complicated by peripheral cholinergic gastrointestinal side effects, especially cramping, nausea, vomiting and diarrhea (Faber et al. Am J Psychiatry 156:1, 1999, page 156—"Faber 1999"). These adverse events were ameliorated by the adjunctive use of the anticholinergic propantheline (Pro-Banthine) at 7.5 mg to 15 mg taken four times a day. Based on these results, the authors recommended adjunctive use of propantheline in patients with untoward gastrointestinal cholinergic effects from cholinesterase inhibitors.

Several reports of benefiting these GI adverse effects with known antiemetics have been published. For example, (See for example Jhee S, Clin Neuropharmacol. 2002 March-April; 25(2):122-3, "Centrally acting antiemetics mitigate nausea and vomiting in patients with Alzheimer's disease who receive rivastigmine"; and Scarzella L, Funct Neurol. 2007 April-June; 22(2):101-4.

Nevertheless, the aforementioned application of the general concept for improving the treatment of dementias of the Alzheimer type provides only limited benefit to patients suffering from these disorders. While potentially lessening side effects, merely employing the concomitant use of antiemetics such as propantheline and domperidone and others fall short of realizing the full therapeutic potential of this acetylcholinesterase approach to the treatment of Alzheimer type dementia. There are several major problems regarding the anticholinergic selected for use by Faber et al.: (1) the duration of action of the antiemetic was too short for current practical use in highly non-compliant demented patients; and (2) none of these reports disclose or suggest that, by reducing adverse events, especially gastrointestinal, it might be possible to increase AChEI dose and thus improve efficacy.

These papers neither mention nor suggest using an antiemetic primarily to raise the AChEI dose and thus improve antidementia efficacy.

In summary, the literature neither discloses nor suggests to take advantage of the side effect mitigation discovered by Faber 1999, achieved with propantheline, or of the nausea/vomiting side effect mitigations achieved with antiemetics to improve the magnitude and/or duration of the otherwise marginal therapeutic response to an AChEI, by allowing to increase the doses of said AChEI and concurrently improving neurobehavioral function and quality of life. No attempt was made in this direction heretofore.

SUMMARY OF THE INVENTION

Considering the results of the above-cited previously published studies in animal models of human cognitive function indicating a dose-response relation between the amount of AChEIs and the degree of cognitive improvement achieved in the clinically relevant dose range, it has been assumed that if dose limiting side effects of AChEIs could be reduced or eliminated, then the administration of higher doses might provide a much needed increase in the size of the therapeutic effect and prolong the duration of drug action, while at the same time having no significant deleterious effect on safety or tolerability.

The therapeutic approach according to the present invention reverses the approach taught by the prior art, in the sense that it provides for an increase of the therapeutic effect of the AChEI (i.e., increase in efficacy) by concurrently globally counteracting their side effects as opposed to combating their side effects without appreciably lessening the central activity of AChEIs, but without increasing their efficacy as taught by the whole prior art.

Thus, it has been found that it is actually possible to maximize the effects of an AChEI in improving the symptoms of Alzheimer type dementia in a patient suffering from said symptoms by administering to said patient said AChEI in combination with a non-anticholinergic antiemetic agent as defined above. For the purposes of this definition, a non-anticholinergic antiemetic drug would have the degree of acetylcholine blockade and the ability to influence the clinical effects of cholinergic receptor stimulation of less than 20 percent of that of atropine and preferably less than 5 percent of that of atropine.

It has also surprisingly been found that by a combined antiemetic/AChEI treatment, the maximization of the cholinomimetic efficacy is achieved with AChEI doses higher than the currently maximal tolerated ones and with antiemetic doses equal to or even lower than those currently used for preventing vomiting.

Finally, it has been found that pharmaceutical compositions comprising a pharmacologically active amount of an AChEI and a pharmacologically active amount of a non-anticholinergic antiemetic agent, in admixture with pharmaceutical carriers, improve the symptoms of Alzheimer type dementia in patients suffering from said symptoms, even in the case of patients who have been withdrawn or are no longer responding to the AChEI therapy because of the severe side-effects, thus assuring not only an improvement of the quality of life of the patients, but also an objective and previously unrealized improvement of their symptoms.

DETAILED DESCRIPTION

The present invention proposes an improved method to augment the efficacy of conventional cholinergic therapies for Alzheimer type dementias by mitigating the common adverse events of cholinomimetic treatments of said Alzheimer type dementias that arise as a result of the concomitant stimulation of cholinergic receptors mediating emesis and emesis-related symptoms at the central vomiting center and chemoreceptor trigger zone as well as at peripheral sites. Non-anticholinergic antiemetic drugs that act to inhibit the nausea/vomiting side effects resulting from cholinomimetic therapy have the potential to reduce the adverse effects, such that higher cholinomimetic doses can be administered leading to higher and more prolonged antidementia efficacy. By combining an extended release cholinomimetic with a non-anticholinergic antiemetic having an advantageous duration of pharmacologic action, in a single dosage form, the benefits to patients of an even longer duration of action is also achieved.

Thus, it is an object of the present invention to provide a method for enhancing the maximal tolerated dose of an acetyl choline esterase inhibitor in a patient suffering from an Alzheimer type dementia without concurrent, appreciable adverse effects, which comprises administering to said patient said AChEI in combination with a non-anticholinergic antiemetic agent, whereby an enhanced acetyl choline esterase inhibition in the CNS of said patient is achieved and the symptoms of an Alzheimer type dementia in said patient are improved.

The invention also provides the use of a non-anticholinergic antiemetic agent for the preparation of pharmaceutical compositions for the treatment of Alzheimer type dementias in combination with an AChEI, whereby the maximal tolerated dose of said AChEI is enhanced, a higher degree of acetyl choline esterase inhibition in the CNS is achieved and the symptoms of Alzheimer type dementia are improved to a greater extent.

The efficacy of non-anticholinergic antiemetic agents in improving the symptoms of Alzheimer type dementia is due to the fact that said antiemetics allow the increase of the therapeutic doses of all the AChEIs up to a factor of 4.

Said AChEIs are those currently used or tested for this indication, such as 1,2,3,4-tetrahydro-9-acridinamine (tacrine), 9-amino-2,3,5,6,7,8-hexahydro-1H-cyclopenta[b]quinoline (ipidacrine); (±)-2,3-dihydro-5,6-dimethoxy-2-[[1-(phenylmethyl)-4-piperidinyl]methyl]-1H-inden-1-one (donepezil) and its pharmaceutically acceptable salts, in particular the hydrochloride, 3-[2-(1-benzyl-4-piperidypethyl]-5,7,-dihydro-6H-pyrrolo[3,2-f]-1,2-benzisoxazol-6-one (icopezil) and its pharmaceutically acceptable salts, in particular the maleate, 3-[1-benzylpiperdin-4-yl]-1-(2,3,4,5-tetrahydro-1H-1-benzazepin-8-yl)propan-1-one (zanapezil) and its pharmaceutically acceptable salts, in particular the fumarate, (S)-N-Ethyl-N-methyl-3-[1-(dimethylamino)ethyl]-phenyl carbamate (rivastigmine) and its pharmaceutically acceptable salts, in particular the hydrogen (2R,3R)-tartrate, 4aS,6R,8aS-3-methoxy-11-methyl-4a,5,9,10,11,12-hexahydroxy-6H-benzofuro[3a,3,2-e,f]benzazepin-6-ol (galantamine) and its pharmaceutically acceptable salts; (1R,9S,13E)-1-amino-13-ethylidene-11-methyl-6-azatricyclo[7.3.1.0$^{2,7}$] trideca-2(7),3,10-trien-5-one (huperzine A) and phenserine and its analogs encompassed by the general formula I

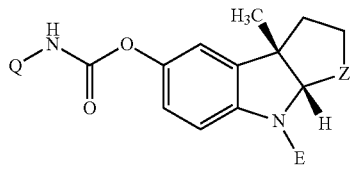

wherein Q is a phenyl group optionally substituted with a $(C_1-C_4)$alkyl or with a methoxy group, Z is an oxygen or sulfur atom or a N-E' radical, E and E', independently, are hydrogen or a methyl group optionally substituted with a phenyl or benzyl group.

Exemplary AChEIs of formula (I), described in U.S. Pat. No. 6,683,105, are phenserine (Q=phenyl; E=$CH_3$; Z=N—$CH_3$); (−)-$N^1,N^8$-bisnorphenserine (Q=phenyl; E=H; Z=N—H); 4'-methoxyphenserine (Q=4'-methoxyphenyl; E=$CH_3$; Z=N—$CH_3$); (−)-$N^1,N^8$-bisbenzylnorphenserine (Q=phenyl; E=$CH_2C_6H_5$; Z=N—$CH_2C_6H_5$); tolserine (Q=o-tolyl; E=$CH_3$; Z=N—$CH_3$); $N^1$-benzylnortolserine (Q=o-tolyl; E=$CH_3$; Z=N—$CH_2$—$C_6H_5$); $N^1$-phenethylnortolserine (Q=o-tolyl; E=$CH_3$; Z=N—$CH_2$—$CH_2$—$C_6H_5$); N'-nortolserine (Q=o-tolyl; E=$CH_3$; Z=N—H); $N^8$-benzylnortolserine (Q=o-tolyl; E=N—$CH_2$—$C_6H_5$; Z=N—$CH_3$); $N^8$-phenethylnortolserine (Q=o-tolyl; E=N—$CH_2$—$CH_2$—$C_6H_5$; Z=N—$CH_3$); $N^8$-nortolserine (Q=o-tolyl; E=H; Z=N—$CH_3$); $N^1,N^8$-bisnortolserine (Q=o-tolyl; E=H; Z=N—H); (−)-N',$N^8$-bisbenzylnortolserine (Q=o-tolyl; E=$CH_2C_6H_5$; Z=N—$CH_2C_6H_5$); cymserine (Q=p-isopropylphenyl; E=$CH_3$; Z=N—$CH_3$); N'-benzylnorcymserine (Q=p-isopropylphenyl; E=$CH_3$; Z=N—$CH_2$—$C_6H_5$); N'-phenethylnorcymserine (Q=p-isopropylphenyl; E=$CH_3$; Z=N—$CH_2$—$CH_2$—$C_6H_5$); N'-norcymserine (Q=p-isopropylphenyl; E=$CH_3$; Z=N—H); $N^8$-benzylnorcymserine (Q=p-isopropylphenyl; E=N—$CH_2$—$C_6H_5$; Z=N—$CH_3$); $N^8$-phenethylnorcymserine (Q=p-isopropylphenyl; E=N—$CH_2CH_2$—$C_6H_5$; Z=N$CH_3$); $N^8$-norcymserine (Q=p-isopropylphenyl; E=H; Z=N—$CH_3$); $N^1,N^8$-bisnorcymserine (Q=p-isopropylphenyl; E=H; Z=N—H); (−)-$N^1,N^8$-bisbenzylnorcymserine (Q=p-isopropylphenyl; E=$CH_2C_6H_5$; Z=N—$CH_2C_6H_5$); thiacymserine (Q=p-isopropylphenyl; E=$CH_3$; Z=S); thiatolserine (Q=o-tolyl; E=$CH_3$; Z=S).

Donepezil hydrochloride, rivastigmine hydrogen (2R,3R)-tartrate and galantamine hydrobromide are the most used AChEIs.

Any antiemetic agent substantially devoid of central anticholinergic effects may be used according to the present invention to improve the efficacy of the AChEIs by allowing an effective increase of their therapeutic doses.

Typical non-anticholinergic antiemetic agents are

5-$HT_3$ receptor antagonists (5HT3-antagonists), such as 9-methyl-3-[(2-methyl-1H-imidazol-1-yl)methyl]-1,2,3,9-tetrahydrocarbazol-4-one (ondansetron) and pharmaceutically acceptable salts and solvates thereof, in particular its hydrochloride dihydrate, described in EP 191562; 3S-ondansetron; 3R-onsdansetron; (3R)-10-oxo-8-azatricyclo[5.3.1.0$^{3,8}$]undec-5-yl 1H-indole-3-carboxylate (dolasetron) and pharmaceutically acceptable salts and solvates thereof, in particular its monomethanesulfonate (mesylate or mesilate) monohydrate, described in EP 266730; 1-methyl-N-(9-methyl-9-azabicyclo[3.3.1]non-3-yl)-indazole-3-carboxamide (granisetron) and pharmaceutically acceptable salts and solvates thereof, in particular its hydrochloride, described in EP 200444; [(1S,5S)-8-methyl-8-azabicyclo[3.2.1]oct-3-yl] 1H-indole-3-carboxylate (tropisetron) and pharmaceutically acceptable salts and solvates thereof, in particular its monohydrochloride, described in U.S. Pat. No. 4,789,673; 1-phenylmethyl-2-piperazinyl-1H-benzimidazole (lerisetron) and pharmaceutically acceptable salts and solvates thereof, in particular its hydrochloride, described in EP 512939; (R)-5-[(1-methyl-3-indolyl)carbonyl]-4,5,6,7-tetrahydro-1H-benzimidazole (ramosetron) and pharmaceutically acceptable salts and solvates thereof, in particular its hydrochloride, described in U.S. Pat. No. 5,344,927; (3aR)-2-[(3S)-1-azabicyclo[2.2.2]oct-3-yl]-2,3,3a,4,5,6-hexahydro-1H-benz[de]isoquinolin-1-one (palonosetron) and pharmaceutically acceptable salts and solvates thereof, in particular its hydrochloride, described in U.S. Pat. No. 5,202,333; 2,3,4,5-tetrahydro-5-methyl-2-[(5-methyl-1H-imidazol-4-yl)methyl]-1H-pyrido[4,3-b]indol-1-one (alosetron) and pharmaceutically acceptable salts and solvates thereof, in particular its hydrochloride, described in U.S. Pat. No. 5,360,800; and (±)-6-chloro-,3,4-dihydro-4-methyl-3-oxo-N-(quinuclidinyl)-2H-1,4-benzoxazine-8-carboxamide (azasetron) and pharmaceutically acceptable salts and solvates thereof, in particular its hydrochloride, described in U.S. Pat. No. 4,892,872; which are known to be serotonin receptors blockers in the central nervous system and gastrointestinal tract and have been proposed for use to treat post-operative and cytotoxic drug nausea and vomiting;

dopamine antagonists ("DA-antagonists"), such as 5-chloro-1-(1-[3-(2-oxo-2,3-dihydro-1H-benzo[d]imidazol-1-yl)propyl]piperidin-4-yl)-1H-benzo[d]imidazol-2(3H)-one (domperidone) and pharmaceutically acceptable salts and solvates thereof, particularly its maleate; 1-[1-[4-(4-fluorophenyl)-4-oxo-butyl]-3,6-dihydro-2H-pyridin-4-yl]-3H-benzoimidazol-2-one (droperidol); 4-[4-(4-chlorophenyl)-4-hydroxy-1-piperidyl]-1-(4-fluorophenyl)-butan-1-one (haloperidol); 3-(2-chloro-10H-phenothiazin-10-yl)-N,N-dimethyl-propan-1-amine (chlorpromazine) and pharmaceutically acceptable salts and solvates thereof, particularly its hydrochloride; 2-chloro-10-[3-(4-methyl-1-piperazinyl)propyl]-10H-phenothiazine (prochlorperazine), and pharmaceutically acceptable salts and solvates thereof, particularly its dimaleate, dimesylate or 1,2-ethanedisulfonate (1:1) (edisilate); dimethyl[1-(10H-phenothiazin-10-yl)propan-2-yl]amine (promethazine) and pharmaceutically acceptable salts and solvates thereof, particularly its hydrochloride; 4-aminosalicylamide and benzamide derivatives like 4-amino-5-chloro-N-[2-(diethylamino)ethyl]-2-methoxybenzamide (metoclopramide) and pharmaceutically acceptable salts and solvates thereof such as its monohydrochloride monohydrate; 4-amino-5-bromo-N-[2-(diethylamino)ethyl]-2-methoxybenzamide (bromopride) and pharmaceutically acceptable salts and solvates thereof, particularly its monohydrochloride and its dihydrochloride monohydrate; 4-amino-N-(1-benzylpiperidin-4-yl)-5-chloro-2-methoxybenzamide (clebopride) and pharmaceutically acceptable salts and solvates thereof, particularly its malate or its hydrochloride monohydrate; N-[(1-allylpyrrolidin-2-yl) methyl]-6-methoxy-1H-benzo[d][1,2,3]triazole-5-carboxamide (alizapride) and pharmaceutically acceptable salts and solvates thereof, particularly its hydrochloride; (L)-2-methoxy-N-((1-propylpyrrolidin-2-yl) methyl)-5-sulfamoylbenzamide (levosulpiride); N-{[4-(2-dimethylaminoethoxy)phenyl]methyl}-3,4,5-trimethoxy-benzamide (trimethobenzamide) and pharmaceutically acceptable salts and solvates thereof, particularly its hydrochloride; which act in the brain and especially at the chemoreceptor trigger zone and are known to be used to treat nausea and vomiting associated with neoplastic disease, radiation sickness, opioids, cytotoxic drugs and general anesthetics;

H1 histamine receptor antagonists ("H1-antagonists"), such as 1-[(4-chlorophenyl)-phenyl-methyl]-4-[(3-methylphenyl)methyl]piperazine (meclizine or meclozine) and pharmaceutically acceptable salts and solvates thereof, particularly its dihydrochloride monohydrate; dimethyl[1-(10H-phenothiazin-10-yl)propan-2-yl] amine (promethazine) and pharmaceutically acceptable salts and solvates thereof, particularly its hydrochloride; 3-(2-chloro-10H-phenothiazin-10-yl)-N,N-dimethyl-propan-1-amine (chlorpromazine) or a salt thereof, particularly its hydrochloride; 2-chloro-10-[3-(4-methyl-1-piperazinyl)propyl]-10H-phenothiazine (prochlorperazine) and pharmaceutically acceptable salts and solvates thereof, particularly its dimaleate, dimesylate or 1,2-ethanedisulfonate (1:1) (edisilate); and 2-(2-{4-[(4-chlorophenyl)(phenyl) methyl]piperazin-1-yl}ethoxy)ethanol (hydroxyzine) and pharmaceutically acceptable salts and solvates thereof such as its hydrochloride or 1,1'-methylene-bis (2-hydroxy-3-naphthalenecarboxylic acid salt (pamoate), which are known to be effective in many conditions, including motion sickness and severe morning sickness in pregnancy;

cannabinoid receptor agonists ("cannabinoids"), such as cannabis; (6aR-trans)-6a,7,8,10a-tetrahydro-6,6,9-trimethyl-3-pentyl-6H-dibenzo[b,d]pyran-1-ol (dronabinol); (6aR,10aR)-rel-3-(1,1-dimethylheptyl)-6,6a,7,8,10,10a-hexahydro-1-hydroxy,6,6-dimethyl-9H-dibenzo[b,d]pyran-9-one (nabilone); and (−)-cis-3-[2-hydroxy-4-(1,1-dimethylheptyp-phenyl]-trans-4-(3-hydroxypropyl)cyclohexanol (CP 55,940); which are known to be used in patients with cachexia and cytotoxic nausea and vomiting;

antagonists of the neurokinine 1 receptor (NK1-antagonists) such as 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one (aprepitant); and (2S,4S)-4-(4-Acetyl-1-piperazinyl)-N-[(1R)-1-[3,5-bis(trifluoromethyl)phenyl] ethyl]-2-(4-fluoro-2-methylphenyl)-N-methyl-1-piperidinecarboxamide (casopitant); which are known to be neurokinine-1 receptors blockers in both the central and peripheral nervous system and have been proposed for use to treat cytotoxic drug nausea and vomiting.

Advantageously, the used non-anticholinergic antiemetic agents are compounds with a duration of action of at least 6 hours, advantageously from 8 to 24 hours, more advantageously from 10 to 24 hours, preferably from 12 to 24 hours, even though non-anticholinergic antiemetics having an appropriate duration of action corresponding to the duration of action of the concomitantly administered AChEI may be successfully used.

According to the present invention, the non-anticholinergic antiemetic agent is administered at doses of from 50% to 300% of the currently recommended IR dose in its antiemetic indication, it being understood that doses of from 50% to 200% will be used in immediate release unit forms while doses of from 75% to 300% will be used in extended release or transdermally applicable unit forms. Such a dose will allow the maximization of the cholinomimetic efficacy with AChEI doses higher than the currently maximal tolerated ones, in particular with doses of AChEIs at least as high as the currently recommended doses and preferably higher than said currently recommended doses, in particular of 100% to 300%, and preferably of 150% or 200% up to or 300% of said recommended dose of AChEI to patients suffering of Alzheimer type dementia without clinically significant symptoms of gastrointestinal distress, particularly anorexia, nausea or vomiting.

According to an embodiment, the non-anticholinergic antiemetic agent to be administered to patients under treatment with an AChEI is a 5HT3-antagonist selected from the group consisting of alosetron and pharmaceutically acceptable salts and solvates thereof, at a daily dose (in alosetron) of from 0.25 mg to 6 mg; dolasetron and pharmaceutically acceptable salts and solvates thereof, at a daily dose (in dolasetron) of from 50 mg to 300 mg; granisetron and pharmaceutically acceptable salts and solvates thereof, at a daily dose (in granisetron) of from 1 mg to 6 mg; ondansetron and pharmaceutically acceptable salts and solvates thereof, at a daily dose (in ondansetron) of from 12 mg to 72 mg; and tropisetron and pharmaceutically acceptable salts and solvates thereof, at a daily dose (in tropisetron) of from 2.5 mg to 15 mg.

According to another embodiment, the non-anticholinergic antiemetic agent to be administered to patients under treatment with an AChEI is a dopamine antagonist selected from the group consisting of domperidone and pharmaceutically acceptable salts and solvates thereof, at a daily dose (in domperidone) of from 15 mg to 90 mg; haloperidol, at a daily dose of from 0.25 mg to 60 mg; chlorpromazine and pharmaceutically acceptable salts and solvates thereof, at a daily dose (in chlorpromazine) of from 25 mg to 450 mg; prochlorperazine and pharmaceutically acceptable salts and solvates thereof, at a daily dose (in prochlorperazine) of from 7.5 mg to 120-150 mg; the 4-aminosalicylamide derivatives metoclopramide and pharmaceutically acceptable salts and solvates thereof, at a daily dose (in metoclopramide) of from 15 mg to 90 mg; bromopride, at a daily dose (in bromopride) of from 10 mg to 180 mg; clebopride and pharmaceutically acceptable salts and solvates thereof, at a daily dose (in clebopride) of from 0.75 mg to 4.5 mg; levosulpiride, at a daily dose of from 37.5 mg to 900 mg; alizapride and pharmaceutically acceptable salts and solvates thereof, at a daily dose (in alizapride) of from 25 mg to 600 mg; and trimethobenzamide and pharmaceutically acceptable salts and solvates thereof, at a daily dose (in trimethobenzamide) of from 450 mg to 3,600 mg.

According to another embodiment, the non-anticholinergic antiemetic agent to be administered to patients under treatment with an AChEI is a H1 histamine receptor antagonist selected from the group consisting of meclizine (also called meclozine) and pharmaceutically acceptable salts and solvates thereof, at a daily dose (in meclizine) of from 12.5 mg to 300 mg; and promethazine and pharmaceutically acceptable salts and solvates thereof, at a daily dose (in promethazine) of from 12.5 mg to 112.5 mg.

According to another embodiment, the non-anticholinergic antiemetic agent to be administered to patients under treatment with an AChEI is a cannabinoid receptor agonist selected from the group consisting of dronabinol, at a daily dose of from 1.25 mg to 60 mg and nabilone, at a daily dose of from 1 mg to 12 mg.

According to another embodiment, the non-anticholinergic agent having antiemetic action to be administered to patients under treatment with an AChEI is a neurokinine 1 receptor antagonist selected from the group consisting of aprepitant, at a daily dose of from 40 mg to 375 mg; and casopitant, at a daily dose of from 25 mg to 450 mg.

According to an advantageous embodiment of the present invention, the non-anticholinergic agent having antiemetic action to be administered to patients under treatment with an AChEI is granisetron or a pharmaceutically acceptable salt thereof in a transdermal device delivering from 2 mg/24 hours to 6 mg/24 hours of granisetron, manufactured according to known techniques, in particular as described for example in U.S. Pat. No. 6,562,363 or in WO 2006/028866.

The administration of the non-anticholinergic agent having antiemetic action to a patient suffering from dementia of Alzheimer type allows the treatment with the maximal recommended doses of an AChEI without clinically significant symptoms of gastrointestinal distress, particularly anorexia, nausea or vomiting and also allows the treatment of said patients with doses higher than the recommended doses, for example with from 1.1 times to 2-3 times the recommended doses, said doses being higher than the maximal AChEI tolerated dose when used alone, thus significantly improving the symptoms of dementia in said patients.

The fact that non-anticholinergic antiemetic agents allow the increase of the maximal tolerated, therapeutic doses of the AChEIs results from a randomized, controlled safety, tolerability, pharmacokinetic and pharmacodynamic study of an AChEI agent alone, such as donepezil, rivastigmine or galantamine, and with a non-anticholinergic antiemetic agent, such as ondansetron, meclizine, prometazine, domperidone, metoclopramide or aprepitant, in normal volunteers.

The protocol is that of a phase 1 study of ascending standard doses of rivastigmine alone (as a representative AChEI), and with ascending standard doses of ondansetron (as a representative non-anticholinergic antiemetic agent) in normal volunteers, to determine the difference between the maximum tolerated dose of rivastigmine as monotherapy and the maximum tolerated dose of rivastigmine coadministered with ondansetron as the primary endpoint, the secondary ones being adverse event profile and drug plasma levels.

Standard approved oral dosage forms of both rivastigmine hydrogen-(2R,3R)-tartrate (simply named rivastigmine in the study) and ondansetron monohydrochloride, dihydrate (simply named ondansetron in the study) are used. The objective: to determine the maximum tolerated dose (MTD), safety and tolerability as well as the pharmacokinetic and pharmacodynamic profile of rivastigmine when administered alone at daily oral doses ranging from 3 mg to 12 mg and together with ondansetron at daily oral doses of up to 24 mg. MTD, for the purposes of this protocol, is defined as the dose of rivastigmine just preceding the one that produced frank vomiting, or intolerable retching, or that is considered medically inappropriate for readministration by the study principal investigator. The ability of any volunteer to withdraw from this study or refuse any medication or procedure is reiterated on a continuing basis.

The volunteers are males and females, who are considered in good general health, aged 18 to 80 years inclusive. No concomitant medications are allowed.

The study will be a randomized, double-blind, placebo-controlled, cross-over and parallel groups, dose-ranging, non-therapeutic, study conducted on volunteers at a single center. The volunteers are evaluated under blinded conditions following randomization to either Group A or Group B.

During the entire study, oral doses of rivastigmine or rivastigmine placebo and ondansetron or ondansetron placebo will be administered simultaneously once daily at about 8 AM for up to 10 days. All subjects will be maintained fasting for the preceding 8 hours (nominally midnight) and until 4 hours after drug administration (nominally noon). Daily doses of rivastigmine begin at 3 mg and range up to 12 mg in increments of 3 mg as deemed medically appropriate. Daily dosing continues until a subject vomits, evidences intolerable retching, refuses further study medications, or the principal investigator terminates further dosing for medical reasons. Daily doses of ondansetron are 24 mg, given once daily at the same time as rivastigmine. In the case of ondansetron intolerance, in the opinion of the principal investigator, the daily dose of ondansetron may be reduced to and maintained at 12 mg.

Volunteers who are randomized to Group A receive single daily doses of rivastigmine starting at 3 mg per day and ascending by 3 mg increments each study day, as tolerated, to a maximum of 12 mg per day. Once the MTD (as defined above) for rivastigmine as monotherapy is determined, simultaneous ondansetron administration begins at a dose of 24 mg per day and continues each study day at this dose. One day after the introduction of ondansetron, rivastigmine administration resumes at the previously determined MTD and rises each study day by increments of 3 mg, as tolerated, to a maximum of 12 mg per day. The study terminates for each volunteer once they have reached their MTD for rivastigmine when administered in combination with ondansetron.

Volunteers who are randomized to Group B first receive ondansetron given once daily at 12 mg and then increased on the second study day to and maintained at 24 mg once daily, as tolerated. Then daily doses of simultaneously administered rivastigmine are introduced, starting at 3 mg and rising in 3 mg increments each study day as tolerated to each subjects' MTD or 12 mg which ever occurs first.

During each study day all subjects receive a constant number of similar appearing rivastigmine or rivastigmine placebo capsules and ondansetron or ondansetron placebo tablets once daily. Both study subjects and Center Staff receive no information concerning drug type or quantity administered at any time during the study. Drugs are administered and compliance assured by an attendant in accordance with orders from a medically qualified investigator. Neither will communicate with study subjects nor those having contact with these subjects.

Drug dosing will be in accordance with the attached Dosing Schedule as considered medically appropriate by the principal investigator. Standard approved oral dosage forms of both rivastigmine and ondansetron will be used. Placebo tablets (or capsules) will have a similar appearance to the active drug tablets (or capsules). All drugs will be administered orally, once daily in the morning at about 0800 hours. On study days, subjects will be kept fasting from 0000 hours (midnight) until at least 4 hours after drug administration (about 1200 hours).

Safety and tolerability are evaluated before, during and after study drug administration by means of reports from subjects as well as by medical staff observations and measurements. Medical procedures including clinical history and physical examination, vital signs and laboratory tests are performed at screening, and at a follow up visit about 7 days after the last drug administration. Some medical procedures are in addition performed each study day.

During each study day, all subjects remain under continuous observation from just before drug administration until 4 hours after drug administration, or until all medically significant study-related abnormalities have subsided. The following tests are performed during each study day: review of systems (focused on known adverse effects of the drugs used), and vital signs (sitting systolic and diastolic blood pressure and radial pulse rate), just before drug dosing and 2 hours thereafter or until any abnormalities have subsided. A 12-lead ECG is obtained on admission and again 2 hours after MTD rivastigmine administration. Laboratory tests include urinalysis and routine evaluations of venous blood samples (including fasting blood sugar, blood urea nitrogen, creatinine, liver transaminases, alkaline phosphatase and bilirubin) on the first and last study days.

The following adverse events are monitored:

(a) Anorexia or nausea, rated daily by a blinded observer during the peak dose period (1 to 2 hours after oral drug administration) in accordance with responses from study subjects during the peak dose period (1 to 2 hours after drug administration) on a numeric scale of 0 (absent) to 5 (very severe).

(b) Retching, rated daily as either absent or present during the peak dose period as witnessed by a blinded observer;

(c) Vomiting, rated daily as either absent or present during the peak dose period as witnessed by a blinded observer; and (d) Others, rated once daily as either absent or present by a blinded observer in accordance with responses from study subjects: diarrhea, abdominal pain, coughing or other respiratory difficulty, chest pain, palpitations, dysuria or other urinary disturbance, blurring of vision, light headedness, syncope, somnolence, agitation, confusion.

For the pharmacokinetic measurements, venous blood samples are collected three times from each subject: (1) at baseline just prior to the first rivastigmine dose, (2) at rivastigmine peak dose 75 minutes after MTD administration and (3) at 4 hours after MTD rivastigmine administration. All specimens are centrifuged, and the serum separated and stored frozen for subsequent assay.

The analysis of primary outcome measure is performed both in study completers and in the intent-to-treat (ITT) population. The ITT population will include all the randomized subjects who have received each of the baseline assessments and at least one post-randomization assessment.

Difference in the MTD of rivastigmine when given alone and together with ondansetron is analyzed using descriptive statistics both within subjects and between subjects assigned to each of the two treatment order groups.

Safety parameters are analyzed to compare differences between the rivastigmine monotherapy and the rivastigmine plus ondansetron treatment groups. These parameters include treatment-emergent adverse events, vital signs, routine laboratory determinations, and ECG measurements.

For the intended use, the non-anticholinergic antiemetic agent is formulated in pharmaceutical compositions comprising, as an active ingredient thereof, said non-anticholinergic antiemetic agent in admixture with a pharmaceutical carrier.

Said composition may be formulated with said pharmaceutical carrier in IR or ER unit forms for oral administration or in unit forms for parenteral, i.e. intramuscular, intravenous, rectal or transdermal, administration.

The non-anticholinergic antiemetic agent is present in an amount that reduces peripherally mediated gastrointestinal adverse effects that would be caused by the administration of a dose of AChEI sufficient to maximally alleviate disease-associated dementia and other neurobehavioral symptoms.

Advantageously, these pharmaceutical compositions comprise the non-anticholinergic antiemetic active ingredient in an amount of from 50% to 300% of the dosage used in the compositions currently used for the treatment of disorders such as nausea, vomiting or motion sickness. The compositions prepared using the non-anticholinergic antiemetic agents according to the present invention allow the maximization of the cholinomimetic efficacy with AChEI doses higher than the currently maximal tolerated ones, in particular by administration of from 1.5 up to three times the recommended dose of AChEI, to patients suffering of Alzheimer type dementia without clinically significant symptoms of gastrointestinal distress particularly anorexia, nausea or vomiting, thus significantly improving the symptoms of dementia.

The compositions are preferably formulated in dosage unit forms for oral or parenteral, in particular transdermal, administration, wherein the non-anticholinergic antiemetic active ingredient is mixed with a pharmaceutical carrier.

The pharmaceutical compositions prepared using the non-anticholinergic antiemetic agents according to the present invention are indicated in the treatment of the symptoms of Alzheimer type dementias in order to improve to a greater extent said symptoms by also allowing an increase of the currently used and also of the maximal tolerated doses of an AChEI, concurrently or sequentially administered therewith, without the side-effects that would hinder said increase of said therapeutic doses.

In said pharmaceutical compositions, the non-anticholinergic antiemetic agent is present in an amount of from 50% to 300% of the amount of said non-anticholinergic antiemetic agent contained in the currently administered IR dosage unit forms for the treatment of disorders such as nausea, vomiting or motion sickness. More particularly, the non-anticholinergic antiemetic agent is present, in an IR unit form, in an amount ranging from 50% to 200% of the amount of said non-anticholinergic antiemetic agent contained in the currently administered IR dosage unit forms for the treatment of the above-cited disorders or, in an ER unit form, in an amount ranging from 75% to 300% of the amount of said non-anticholinergic antiemetic agent contained in the currently administered unit dosage IR forms for the treatment of the above-cited disorders.

An advantageous non-anticholinergic antiemetic agent in said pharmaceutical compositions is selected from the group consisting of alosetron and pharmaceutically acceptable salts and solvates thereof, in an amount (in alosetron) of from 0.25 mg to 3 mg; dolasetron and pharmaceutically acceptable salts thereof, in an amount (in dolasetron) of from 25 mg to 300 mg; granisetron and pharmaceutically acceptable salts thereof, in an amount (in granisetron) of from 0.5 mg to 3 mg; ondansetron and pharmaceutically acceptable salts and solvates thereof, in an amount (in ondansetron) of from 2 mg to 24 mg; tropisetron and pharmaceutically acceptable salts thereof, in an amount (in tropisetron) of from 2.5 mg to 15 mg; domperidone and pharmaceutically acceptable salts and solvates thereof, in an amount (in domperidone) of from 5 mg to 30 mg; haloperidol, in an amount of from 0.5 mg to 30 mg; chlorpromazine and pharmaceutically acceptable salts and solvates thereof, in an amount (in chlorpromazine) of from 12.5 mg to 300 mg; prochlorperazine and pharmaceutically acceptable salts and solvates thereof, in an amount of from 2.5 mg to 30 mg; metoclopramide and pharmaceutically acceptable salts and solvates thereof, in an amount (in metoclopramide) of from 5 mg to 30 mg; bromopride and pharmaceutically acceptable salts and solvates thereof, in an amount (in bromopride) of from 5 mg to 30 mg; clebopride and pharmaceutically acceptable salts thereof, in an amount (in clebopride) of from 0.25 mg to 1.5 mg; levosulpiride, in an amount of from 12.5 mg to 300 mg; alizapride and pharmaceutically acceptable salts thereof, in an amount (in alizapride) of from 25 mg to 150 mg; trimethobenzamide and pharmaceutically acceptable salts and solvates thereof, in an amount (in trimethobenzamide) of from 150 mg to 900 mg; meclizine (also called meclozine) and pharmaceutically acceptable salts and solvates thereof, in an amount (in meclizine) of from 6.25 mg to 150 mg; promethazine and pharmaceutically acceptable salts thereof, in an amount (in promethazine) of from 12.5 mg to 150 mg; dronabinol, in an amount of from 1.25 mg to 30 mg; nabilone, in an amount of from 0.25 mg to 3 mg; aprepitant, in an amount of from 20 mg to 375 mg; and casopitant, in an amount of from 25 mg to 150 mg.

According to an advantageous embodiment, the pharmaceutical compositions prepared by using the non-anticholinergic antiemetics according to the present invention are present in unit forms also containing other active ingredients, in particular an AChEI which acts as cholinergic agent in the CNS to improve the symptoms of Alzheimer type dementia, in a quantity sufficient to maximally alleviate disease-associated neurobehavioral symptoms, with a minimum of treatment-associated adverse effects.

Thus, it is another object of the present invention to provide a pharmaceutical unit form which comprises
(a) a non-anticholinergic antiemetic agent; and
(b) an AChEI
in admixture with a pharmaceutical carrier.

In the pharmaceutical unit form of the present invention, the non-anticholinergic antiemetic agent Component (a), is present in an amount of from 50% to 300% of the amount of the said non-anticholinergic antiemetic agent contained as a sole active ingredient in the currently used brand or generic drugs.

According to a preferred embodiment, said Component (a) is a non-anticholinergic antiemetic agent selected from the group consisting of (a1) 5HT3-antagonists, (a2) DA-antagonists, (a3) H1-antagonists, (a4) cannabinoids, (a5) aprepitant and (a6) casopitant.

The pharmaceutical composition to improve the treatment of human dementias of the Alzheimer type according to the present invention may comprise a mixture of a non-anticholinergic antiemetic agent, Component (a), and of an AChEI, Component (b), wherein Component (b) is present in a quantity sufficient to maximally alleviate disease-associated neurobehavioral symptoms and wherein Component (a) is present in a second quantity that reduces adverse effects that would be caused by the AChEI if administered without the accompanying non-anticholinergic antiemetic agent.

Said amount of Component (b) sufficient to maximally alleviate disease-associated cognitive and other neurobehavioral symptoms is from 1 time to 3 times, advantageously 1.5 times to 3 times, preferably 2-3 times the maximal dose contained in the currently used brand or generic AChEIs.

As to Component (a), typical 5HT3-antagonist non-anticholinergic antiemetic agents (a1) are the compounds described in EP 191562, in particular ondansetron and pharmaceutically acceptable salts and solvates thereof; the compounds described in EP 200444, in particular granisetron and pharmaceutically acceptable salts and solvates thereof; the compounds described in EP 266730, in particular dolasetron and pharmaceutically acceptable salts and solvates thereof; the compounds described in U.S. Pat. No. 4,789,673, in particular tropisetron and pharmaceutically acceptable salts and solvates thereof; and the compounds described in EP 430190, in particular palonosetron and pharmaceutically acceptable salts and solvates thereof.

Typical DA-antagonists (a2) are domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; and 4-aminosalicylamide derivatives such as metoclopramide and pharmaceutically acceptable salts and solvates thereof such as the hydrochloride monohydrate, bromopride and pharmaceutically acceptable salts and solvates thereof such as the monohydrochloride or the dihydrochloride monohydrate, alizapride and pharmaceutically acceptable salts and solvates thereof such as the hydrochloride, and clebopride and pharmaceutically acceptable salts and solvates thereof such as the malate and the hydrochloride monohydrate.

Typical histamine H1 receptor antagonists (a3) are meclizine (meclozine) and pharmaceutically acceptable salts and solvates thereof such as the hydrochloride monohydrate; promethazine and pharmaceutically acceptable salts and solvates thereof such as the hydrochloride; chlorpromazine and pharmaceutically acceptable salts and solvates thereof such as the hydrochloride, prochlorperazine and pharmaceutically acceptable salts and solvates thereof such as the dimaleate, the dimesylate or the 1,2-ethanedisulfonate (1:1) (edisilate); hydroxyzine and pharmaceutically acceptable salts and solvates thereof such as the dihydrochloride or the 1,1'-methylene bis(2-hydroxy-3-naphthalenecarboxylic acid (pamoate) salt.

Typical cannabinoids (a4) are nabilone and dronabinol.

Each of said typical non-anticholinergic antiemetic agents is present in the pharmaceutical composition, as Component (a), in an amount ranging from 50% of the minimum amount to 300% of the maximum amount of said typical non-anticholinergic antiemetic agent contained in the corresponding, currently used generic or brand drug for its antiemetic indication in IR form.

Advantageous Component (a) is selected from the group consisting of alosetron and pharmaceutically acceptable salts and solvates thereof, in particular the hydrochloride, in an amount (in alosetron) of from 0.25 mg to 3 mg; dolasetron and pharmaceutically acceptable salts and solvates thereof, in particular the mesylate, in an amount (in dolasetron) of from 25 mg to 300 mg; granisetron and pharmaceutically acceptable salts and solvates thereof, in particular the hydrochloride, in an amount (in granisetron) of from 0.5 mg to 3 mg; ondansetron and pharmaceutically acceptable salts and solvates thereof, in particular the hydrochloride dihydrate, in an amount (in ondansetron) of from 2 mg to 24 mg; tropisetron and pharmaceutically acceptable salts and solvates thereof, in particular the hydrochloride, in an amount of from 2.5 mg to 15 mg; domperidone and pharmaceutically acceptable salts and solvates thereof, in an amount (in domperidone) of from 5 mg to 30 mg; haloperidol, in an amount of from 0.5 mg to 30 mg; chlorpromazine and pharmaceutically acceptable salts and solvates thereof, in particular the hydrochloride, in an amount (in chlorpromazine) of from 12.5 mg to 75 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 30 mg; bromopride and pharmaceutically acceptable salts and solvates, in particular the monohydrochloride and the dihydrochloride monohydrate, in an amount (in bromopride) of from 5 mg to 30 mg; clebopride and pharmaceutically acceptable salts and solvates thereof, in particular the hydrogen malate and the hydrochloride monohydrate, in an amount (in clebopride) of from 0.25 mg to 1.5 mg; levosulpiride, in an amount of from 12.5 mg to 300 mg; alizapride and pharmaceutically acceptable salts thereof, in particular the hydrochloride, in an amount (in alizapride) of from 25 mg to 150 mg; trimethobenzamide and pharmaceutically acceptable salts thereof such as the monohydrochloride, in an amount (in trimethobenzamide) of from 150 mg to 900 mg; meclizine (also called meclozine) and pharmaceutically acceptable salts and solvates thereof, in an amount (in meclizine) of from 6.25 mg to 150 mg; promethazine and pharmaceutically acceptable salts and solvates thereof, in particular the hydrochloride, in an amount (in prometazine) of from 12.5 mg to 150 mg; dronabinol in an amount of from 1.25 mg to 60 mg; nabilone, in an amount of from 1 mg to 12 mg; aprepitant, in an amount of from 20 mg to 375 mg; and casopitant, in an amount of from 25 mg to 150 mg.

Preferred Component (a) is selected from the group consisting of ondansetron and pharmaceutically acceptable salts and solvates thereof, in an amount (in ondansetron) of from 2 mg to 24 mg; granisetron and pharmaceutically acceptable salts and solvates thereof, in an amount (in granisetron) of from 0.5 mg to 3 mg; domperidone and pharmaceutically acceptable salts and solvates thereof, in an amount (in domperidone) of from 5 mg to 30 mg; metoclopramide and pharmaceutically acceptable salts and solvates thereof, in an amount (in metoclopramide) of from 5 mg to 30 mg; dronabinol, in an amount of from 1.25 mg to 30 mg; nabilone, in an amount of from 0.25 mg to 3 mg; aprepitant, in an amount of from 20 mg to 375 mg; and casopitant, in an amount of from 25 to 150 mg.

As to Component (b), typical AChEIs are 1,2,3,4-tetrahydro-9-acridinamine (tacrine), 9-amino-2,3,5,6,7,8-hexahydro-1H-cyclopenta[b]quinoline (ipidacrine); (±)-2,3-dihydro-5,6-dimethoxy-2-[[1-(phenylmethyl)-4-piperidinyl]methyl]-1H-inden-1-one (donepezil) and its pharmaceutically acceptable salts, (5)-N-Ethyl-N-methyl-3-[1-(dimethylamino)ethyl]-phenyl carbamate (rivastigmine) and its pharmaceutically acceptable salts, 4aS ,6R,8aS-3 -mthoxy-11-methyl-4a,5,9,10,11,12-hexahydroxy-6H-benzofuro[3a,3 ,2-e,f]benzazepin-6-ol (galantamine) and its pharmaceutically acceptable salts; (1R,9S,13E)-1-amino-13 -ethylidene-11-methyl-6-azatricyclo[7.3.1.0$^{2,7}$]trideca-2(7), 3,10-trien-5-one (huperzine A) and phenserine and its analogs encompassed by the general formula I.

Advantageous AChEIs include those now part of standard care for patients suffering from a dementia of the Alzheimer type and that are also widely used off-label for various other chronic progressive disorders of cognitive function. AChEIs have as a general mechanism of action the enhancement of acetylcholine-mediated neurotransmission. All act in the human CNS to increase and prolong the availability of acetylcholine by inhibiting its degradatory enzyme acetylcholinesterase, such as tacrine; huperzine A; donepezil; pharmaceutically acceptable salts of donepezil, especially the hydrochloride thereof; icopezil; pharmaceutically acceptable salts of icopezil, especially the maleate thereof; zanapezil; pharmaceutically acceptable salts of zanapezil, especially the fumarate thereof; rivastigmine; pharmaceutically acceptable salts of rivastigmine, especially the hydrogen tartrate thereof; galantamine; pharmaceutically acceptable salts of galantamine especially the hydrobromide thereof.

Preferred Component (b) is an AChEI selected from the group consisting of tacrine; huperzine A; donepezil and pharmaceutically acceptable salts thereof, in particular its hydrochloride; rivastigmine and pharmaceutically acceptable salts thereof, in particular its hydrogen-(2R,3R)-tartrate (rivastigmine tartrate); galantamine and pharmaceutically acceptable salts thereof, in particular its hydrobromide; the group consisting of the last three AChEIs and of their pharmaceutically acceptable salts being particularly preferred. As set forth above, these AChEIs vary in their pharmacological profiles and in their affinities for acetylcholinesterase and butyrylcholinesterase.

The dose of the Component (b) may vary according to intrinsic acetylcholine esterase inhibiting potency of said component. Advantageously, said dose is from 1.5-fold to more than twice higher than the maximal one currently used when the same AChEI is alone.

In the unit forms of the present invention, for immediate release or extended release, the antiemetic Component (a) is present in an amount of from 50% to 300% of the amount of said antiemetic contained in the currently administered IR dosage unit forms for the treatment of disorders such as emesis or motion sickness and the AChEI Component (b) is present in an amount of from 100% to 300% of the amount of said AChEI contained in the currently administered IR dosage unit forms for the treatment of Alzheimer type dementia.

More particularly, the non-anticholinergic antiemetic is present, in an IR unit form, in an amount ranging from 50% to 200% of the maximum amount of said antiemetic agent contained in the currently administered IR dosage unit forms for the treatment of the above-cited disorders or, in an ER unit form, in an amount ranging from 75% to 300% of the currently administered IR dosage unit forms for the treatment of the above-cited disorders.

For example, among the advantageous non-anticholinergic antiemetic agents used as Component (a), ondansetron or a pharmaceutically acceptable salt or solvate thereof, in particular its hydrochloride dihydrate, is present in an amount (in ondansetron) of from 2 mg to 16 mg per dosage unit in an IR unit form or in an amount of from 3 mg to 24 mg, preferably from 8 mg to 24 mg, in an ER unit form; alosetron or a pharmaceutically acceptable salt thereof, in particular its hydrochloride, is present in an amount (in alosetron) of from 0.25 mg to 2 mg per dosage unit in an IR unit form or in an amount of from 0.375 mg to 3 mg, preferably from 1 mg to 3 mg, in an ER unit form; tropisetron or a pharmaceutically acceptable salt thereof, in particular its hydrochloride, is present in an amount (in tropisetron) of from 2.5 mg to 10 mg per dosage unit in an IR unit form or in an amount of from 3.75 mg to 15 mg, preferably from 5 mg to 24 mg, in an ER unit form; granisetron or a pharmaceutically acceptable salt thereof, in particular its hydrochloride, is present in an amount (in granisetron) of from 0.5 mg to 2 mg per dosage unit in an IR unit form or in an amount of from 0.75 mg to 3 mg, preferably from 1 mg to 3 mg, in an ER unit form; dolasetron, or a pharmaceutically acceptable salt thereof, in particular its mesilate, is present in an amount (in dolasetron) of from 25 mg to 200 mg per dosage unit in an IR unit form or in an amount of from 37.5 mg to 300 mg, preferably from 100 mg to 300 mg, in an ER unit form; domperidone or a pharmaceutically acceptable salt thereof, in particular its maleate, is present in an amount (in domperidone) of from 5 mg to 20 mg per dosage unit in an IR unit form or in an amount of from 7.5 mg to 60 mg, preferably from 10 mg to 60 mg, in an ER unit form; metoclopramide or a pharmaceutically acceptable salt or solvate thereof, in particular its monohydrochloride monohydrate, is present in an amount (in metoclopramide) of from 5 mg to 20 mg per dosage unit in an IR unit form or in an amount of from 7.5 mg to 30 mg, preferably from 10.0 mg to 30.0 mg, in an ER unit form; alizapride or a pharmaceutically acceptable salt thereof, in particular its hydrochloride, is present in an amount (in alizapride) of from 25 mg to 100 mg per dosage unit in an IR unit form or in an amount of from 37.5 mg to 300 mg, preferably from 100 mg to 300 mg, in an ER unit form; meclizine or a pharmaceutically acceptable salt thereof, in particular its hydrochloride is present in an amount (in meclizine) of from 6.25 mg to 100 mg per dosage unit in an IR unit form or in an amount of from 37.5 mg to 150 mg, preferably from 50 mg to 150 mg, in an ER unit form; chlorpromazine or a pharmaceutically acceptable salt thereof, in particular its hydrochloride is present in an amount (in chlorpromazine) of from 12.5 mg to 200 mg per dosage unit in an IR unit form or in an amount of from 75 mg to 300 mg, preferably from 150 mg to 300 mg, in an ER unit form; prochlorperazine or a pharmaceutically acceptable salt thereof, in particular its maleate is present in an amount (in prochlorperazine) of from 6.25 mg to 100 mg per dosage unit in an IR unit form or in an amount of from 37.5 mg to 150 mg, preferably from 50 mg to 150 mg, in an ER unit form; dronabinol is present in an amount of from 1.25 mg to 20 mg per dosage unit in an IR unit form or in an amount of from 1.8 mg to 60 mg, preferably from 2.5 mg to 60 mg, in an ER unit form; nabilone is present in an amount of from 0.25 mg to 2 mg per dosage unit in an IR unit form or in an amount of from 0.75 mg to 3 mg per dosage unit in an IR unit form; aprepitant is present in an amount of from 20 mg to 250 mg per dosage unit in an IR unit form or in an amount of from 30 mg to 750 mg, preferably from 125 mg to 500 mg, in an ER unit form; and casopitant is present in an amount of from 25 mg to 150 mg per dosage unit in an IR unit form.

Preferred Component (a) is a non-anticholinergic antiemetic agent selected from the group consisting of ondansetron and pharmaceutically acceptable salt and solvated thereof, in an amount (in ondansetron) of from 2 mg to 24 mg; granisetron and pharmaceutically acceptable salt and solvates thereof, in an amount (in granisetron) of from 0.5 mg to 3 mg; domperidone and pharmaceutically acceptable salts and solvates thereof, in an amount (in domperidone) of from 5 mg to 30 mg; metoclopramide and pharmaceutically acceptable salts and solvates thereof, in an amount (in metoclopramide) of from 5 mg to 30 mg; dronabinol, in an amount of from 1.25 mg to 30 mg; nabilone, in an amount of from 0.25 mg to 3 mg; aprepitant, in an amount of from 20 mg to 375 mg; and casopitant, in an amount of from 25 mg to 150 mg.

In unit forms for immediate release or extended release, the AChEI Component (b) is present in an amount of from 100% to 300% of the amount of said AChEI contained in the currently administered IR or ER dosage unit forms for the treatment of Alzheimer type dementia.

More particularly the AChEI Component (b) is present in an IR unit form, in an amount ranging from about 100% to about 300%, preferably from 150% to 300%, of the amount of said AChEI contained in the currently administered IR dosage unit forms for the palliative treatment of Alzheimer type dementia or, in an ER unit form, in an amount ranging from 150% to 300%, preferably from 200% to 300%, of the amount of said AChEI contained in the currently administered unit dosage IR forms for the treatment of Alzheimer type dementia.

For example, according to the present invention, among the preferred Components (b), tacrine is present in amount of from 5 mg to 120 mg, advantageously from 40 mg to 120 mg, preferably from 60 mg to 120 mg per dosage unit; huperzine A is present in an amount of from 50 µg to 150 µg, advantageously from 75 µg to 150 µg, preferably from 100 µg to 150 µg per dosage unit; donepezil or a pharmaceutically acceptable salt thereof, preferably the hydrochloride, is present in an amount (in donepezil) of from 10 mg to 30 mg, preferably from 15 mg to 30 mg, per dosage unit; rivastigmine or a pharmaceutically acceptable salt thereof, preferably the hydrogen tartrate, is present in an amount (in rivastigmine) of from 6 mg to 18 mg, preferably from 9 mg to 18 mg per dose unit; and galantamine, or a pharmaceutically acceptable salt thereof, preferably the hydrobromide, is present in an amount (in galantamine) of from 12 mg to 36 mg, preferably from 16 mg to 36 mg per dosage unit.

Advantageously, said AChEI can be administered in a dose that is higher than the maximal tolerated dose of the same AChEI when administered alone and will preferably be from 1.5 to 3 times higher than the currently recommended doses in the treatment of Alzheimer type dementia.

The unit form of the present invention may be a tablet, a capsule, a pre-measured volume of a liquid solution or suspension for oral administration or a patch for transdermal application. In said unit form the antiemetic agent and the AChEI may be mixed together or separated according to known technologies in admixture with a pharmaceutical carrier in a pharmaceutical composition.

Component (a) and Component (b) are formulated with conventional pharmaceutical carriers in known formulations for oral use wherein said components are mixed together or separated, for example in two tablets introduced in a capsule or in a two-compartment capsule or in a multilayer (di-layer) tablet wherein the two components are both in IR or in ER form or one of the two components is in IR form and the other is in ER form, according to known technologies.

The pharmaceutical carriers and vehicles are those commonly used for the preparation of compositions for oral, buccal and parenteral, in particular transdermal, administration. Appropriate unit forms comprise the oral forms such as tablets, soft or hard gelatin capsules, powders or granulates in sachets and suitably measured oral solutions or suspensions as well as patches for transdermal administration.

Component (a) and Component (b) may also be present in form of one of their complexes with a cyclodextrin, for example α-cyclodextrin, β-cyclodextrin, β-cyclodextrin, 2-hydroxypropyl-β-cyclodextrin or methyl-β-cyclodextrin.

Component (a) and Component (b) may also be formulated in the form of microcapsules, optionally with one or more carriers or additives.

For oral administration, Component (a) and Component (b), together or separately, are formulated by mixing the active ingredient with conventional pharmaceutical acceptable carriers enabling said active ingredients to be formulated in tablets, dragees, orally disintegrating tablets, capsules, liquid solutions or suspensions, syrups and the like.

Carriers for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubrifiants such as polyethylenglycol or magnesium stearate; ligands such as methylcellulose, sodium carboxymethylcellulose, alginic acid, alginates; sweeteners, such as saccharose, dextrose, mannitol, saccharin; or flavoring agents such as natural or synthetic oils.

Carriers for orally disintegrating tablets include for example lubricants, aggregating, sweetening, flavoring or disaggregating agents as well as agents improving the buccal mucosa absorption of Components (a) and (b) such as sorbitol, mannitol, lactose and cellulose.

Carriers for liquid, normally aqueous, suspensions or solutions include for example antioxidants, such as sodium metabisulfite or sodium sulfite, thickening agents, such as microcrystalline cellulose, hydroxypropylcellulose, carboxymethylcellulose or polyvinylpyrrolidone, preservatives such as methyl paraben, ethyl paraben, sodium ethylenediaminotetracetate, sodium benzoate or an alkaline salt of sorbic acid, as well as flavoring and sweetening agents.

The sweeteners contained in the orally disintegrating tablets and the liquid suspensions or solutions may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

The composition according to the present invention may be in form of a capsule containing two tablets as described herein above, one of them comprising Component (a) and the other comprising Component (b).

The association of a non-anticholinergic antiemetic and an AChEI may be formulated in tablets in which one or both of the two components is in controlled-release formulation, for example as a dispersion of said component in hydroxypropyl methyl cellulose or in a film-coated microgranule. Advantageously, the AChEI, in a ER-formulation is in the core and the non-anticholinergic antiemetic agent, in IR-formulation, is in the outer layer in multi-layer tablets in which, for example, both the core and the outer layer are coated with a film. Analogously, capsules made of two separated parts, one containing Component (a), in IR- or ER-formulation and the other containing Component (b), in IR- or ER-formulation, may be used Carriers and vehicles for ER tablets include retardant materials such as is acrylic and methacrylic acid polymers and copolymers; cellulose derivatives such as hydroxypropylmethylcellulose, hydroxyethylcellulose, hydroxypropylethylcellulose, hydroxypropylcellulose, methylcellulose, ethylcellulose, or sodium carboxymethylcellulose; gums; waxes; glycerides or aliphatic alcohols or a mixture thereof.

In particular, the unit forms of the present invention comprise a non-anticholinergic antiemetic agent selected from the group consisting of ondansetron and the pharmaceutically acceptable salts and solvates thereof, in an amount (in ondansetron) of from 2 mg to 24 mg; granisetron and the pharmaceutically acceptable salts and solvates thereof, in an amount (in granisetron) of from 0.5 mg to 3 mg; dolasetron and the pharmaceutically acceptable salts and solvates thereof, in an amount (in dolasetron) of from 25 mg to 300 mg; domperidone and the pharmaceutically acceptable salts and solvates thereof, in an amount (in domperidone) of from 5 mg to 30 mg; metoclopramide and the pharmaceutically acceptable salts and solvates thereof, in an amount (in metoclopramide) of from 5 mg to 30 mg; alizapride and the pharmaceutically acceptable salts thereof, in an amount (in alizapride) of from 25 mg to 150 mg; dronabinol, in an amount of from 1.25 mg to 30 mg per dosage unit; nabilone, in an amount of from 1 mg to 12 mg; aprepitant in an amount of from 20 mg to 375 mg; and casopitant in an amount of from 25 mg to 150 mg, as Component (a); and a member selected from the group consisting of tacrine, in an amount of from 10 mg to 120 mg, advantageously of from 40 mg to 120 mg preferably of from 60 mg to 120 mg; huperzine A, in an amount of from 50 µg to 150 µg, advantageously of from 75 µg to 150 µg, preferably from 100 µg to 150 µg; donepezil and pharmaceutically acceptable salts thereof, in an amount (in donepezil) of from 5 mg to 30 mg, advantageously of from 10 mg to 30 mg, preferably from 15 mg to 30 mg; rivastigmine and its pharmaceutically acceptable salts, in an amount (in rivastigmine) of from 1.5 mg to 18 mg advantageously of from 6 mg to 18 mg, preferably from 9 mg to 18 mg; and galantamine and its pharmaceutically acceptable salts, in an amount, in galantamine, of from 4 mg to 36 mg advantageously of from 12 mg to 36 mg, preferably from 16 mg to 36 mg; as Component (b), in admixture with a pharmaceutical carrier.

Preferred units forms comprise
(a) a non-anticholinergic antiemetic agent selected from the group consisting of ondansetron and pharmaceutically acceptable salts and solvates thereof, in an amount (in ondansetron) of from 2 mg to 16 mg; granisetron and pharmaceutically acceptable salts and solvates thereof, in an amount (in granisetron) of from 0.5 mg to 2 mg; domperidone and pharmaceutically acceptable salts and solvates thereof, in an amount (in domperidone) of from 5 mg to 20 mg; metoclopramide and pharmaceutically acceptable salts and solvates thereof, in an amount (in metoclopramide) of from 5 mg to 20 mg; dronabinol, in an amount of from 1.25 mg to 20 mg; nabilone, in an amount of from 0.25 mg to 2 mg; aprepitant, in an amount of from 20 mg to 250 mg; and casopitant, in an amount of from 25 mg to 100 mg; and
(b) an AChEI selected from the group consisting of donepezil and pharmaceutically acceptable salts thereof, in an amount (in donepezil) of from 15 mg to 30 mg; rivastigmine and pharmaceutically acceptable salts thereof, in an amount (in rivastigmine) of from 9 mg to 18 mg; and galantamine and pharmaceutically acceptable salts thereof, in an amount (in galantamine) of from 16 mg to 36 mg;
in admixture with a pharmaceutical carrier.

Such unit forms, formulated as IR oral compositions, are particularly preferred.

According to an embodiment, the compositions of the present invention are formulated by mixing the Component (a) and the Component (b) together, in admixture with a pharmaceutical carrier for an immediate or extended release. An advantageous composition according to this embodiment comprises an amount of granisetron hydrochloride corresponding to from 0.5 mg to 2 mg of granisetron , as Component (a); and
    from 10 mg to 20 mg, preferably from 15 mg to 20 mg, of donepezil (as hydrochloride); or
    from 6 mg to 18 mg, preferably from 9 mg to 18 mg, of rivastigmine (as hydrogen tartrate); or
    from 12 mg to 24 mg, preferably from 18 mg to 24 mg, of galantamine (as hydrobromide),
as Component (b), wherein Components (a) and (b) are mixed together and with a pharmaceutical carrier in an IR-formulation, said composition being destined to be administered once or twice per day.

According to another embodiment, the compositions of the present invention are formulated by mixing the Component (a) with a pharmaceutical carrier for an immediate or extended release in tablets (Tablet A) and the Component (b), separately, with a pharmaceutical carrier for an immediate or extended release in tablets (Tablet B) and introducing Tablet A and Tablet B in a capsule for oral administration as described for example in GB 1204580 or in US 2007/0224259. An advantageous composition according to this embodiment consists of soft or hard gelatin capsules each containing Tablet A comprising an amount of dolasetron mesylate hydrate equivalent to from 25 mg to 200 mg of dolasetron, as Component (a), in admixture with a pharmaceutical carrier in a IR formulation; and Tablet B, comprising
    from 10 mg to 20 mg, preferably from 15 mg to 20 mg, of donepezil (as hydrochloride); or
    from 6 mg to 18 mg, preferably from 9 mg to 18 mg, of rivastigmine (as hydrogen tartrate); or
    from 12 mg to 24 mg, preferably from 18 mg to 24 mg, of galantamine (as hydrobromide),
as Component (b), with a pharmaceutical carrier in an IR-formulation, said composition being destined to be administered once or twice per day.

According to a further embodiment, the compositions according to the present invention are formulated in a di-layer tablet which releases two drug doses, in which the release of a drug from one drug-containing layer does not interfere with the release of a drug from the other drug-containing layer as described for example in WO 2006/089493. An advantageous composition according to this embodiment consists of
Layer A, comprising an amount of ondansetron hydrochloride dihydrate equivalent to from 8 mg to 16 mg, preferably from 12 mg to 16 mg, of ondansetron, as Component (a), with a pharmaceutical carrier in a IR formulation and
Layer B, comprising 12 mg to 24 mg, preferably from 18 mg to 24 mg of galantamine (as hydrobromide),
as Component (b), in admixture with a pharmaceutical carrier in an IR-formulation, said composition being destined to be administered once or twice per day.

According to another embodiment, the compositions of the present invention are formulated in oral disintegrable tablets. Particularly advantageous compositions according to this embodiment are orally disintegrable tablets comprising
    an amount of ondansetron hydrochloride dihydrate equivalent to from 8 mg to 16 mg, preferably from 12 mg to 16 mg, of ondansetron, as Component (a); and
    from 10 mg to 20 mg, preferably from 15 mg to 20 mg, of donepezil hydrochloride, as Component (b),
in admixture with a pharmaceutical carrier in an IR-formulation for buccal mucosa absorption, said composition being destined to be administered once or twice per day.

According to another embodiment, the compositions of the present invention are formulated in solutions for oral administration wherein Component (a) and Component (b) are dissolved or suspended in water in admixture with conventional carrier or vehicles. Particularly advantageous compositions according to this embodiment are oral solutions or suspensions, each unit form thereof comprising
    a Component (a) selected from the group consisting of ondansetron (as hydrochloride dihydrate) in an amount of from 8 mg to 16 mg, preferably from 12 mg to 16 mg; domperidone (as maleate) in an amount of from 10 mg to 20 mg, preferably from 15 mg to 20 mg; and metoclopramide (as hydrochloride monohydrate) in an amount of 10 mg to 20 mg, preferably from 15 mg to 20 mg; and
    from 12 mg to 24 mg, preferably from 18 mg to 24 mg, of galantamine (as hydrobromide), as Component (b),
in admixture with a pharmaceutical carrier in a liquid IR-formulation for oral administration, said composition being destined to be administered, in said dosage unit form, once or twice per day.

According to another embodiment, the compositions of the present invention are formulated in patch for transdermal administration. Particularly advantageous compositions according to this embodiment are transdermal patch formulations comprising
    from 2 mg/24 hours to 6 mg/24 hours of granisetron (as hydrochloride), as Component (a); and
    from 10-15 mg/24 hours to 24 mg/24 hours of rivastigmine (as hydrogen tartrate), as Component (b),
with a pharmaceutically acceptable carrier or diluent which is suitable for systemic transdermal administration.

Another embodiment of the present invention provides units forms consisting of tablets comprising from 10 mg to 20 mg, preferably from 15 mg to 20 mg of metoclopramide (as hydrochloride monohydrate), as Component (a); and from 12 mg to 24 mg, preferably from 18 mg to 24 mg, of galantamine (as hydrobromide), as Component (b), in admixture with a pharmaceutical carrier in a IR-formulation for oral administration, said composition being destined to be administered once or twice per day.

Another embodiment of the present invention provides units forms consisting of tablets comprising from 10 mg to 20 mg, preferably from 15 mg to 20 mg, of domperidone (as maleate), as Component (a); and from 6 mg to 18 mg, preferably from 9 mg to 18 mg, of rivastigmine (as hydrogen tartrate), as Component (b), in admixture with a pharmaceutical carrier in a IR-formulation for oral administration, said composition being destined to be administered once or twice per day.

A particularly advantageous embodiment of the present invention provides units forms consisting of capsules comprising from 40 mg to 250 mg, preferably from 80 mg to 250 mg, of aprepitant, as Component (a); and from 15 mg to 30 mg, preferably from 20 mg to 30 mg, of donepezil (as hydrochloride), as Component (b), in admixture with a pharmaceutical carrier in a IR-formulation for oral administration, said composition being destined to be administered once a day.

As compared to known drugs of the acetylcholine esterase inhibitor type now used alone in the treatment of Alzheimer type dementias, the above combined pharmaceutical compositions show greater and longer efficacy and less adverse effects by allowing the safe and tolerable administration of larger and thus more therapeutically effective quantities of said acetylcholine esterase inhibitor. In particular, the acetylcholine esterase inhibitor of the pharmaceutical compositions of the present invention is safe and effective, alone or in combination with other pharmaceuticals, in treating patients in need of an acetylcholine esterase inhibition, in particular dementias of the Alzheimer type on a once or twice daily basis.

The pathologic conditions treated with the composition of the present invention include, but are not limited to, Alzheimer's disease, Parkinson's disease dementia, and other disorders of human cognitive and neurobehavioral function that are treated, in part, by pharmaceuticals intended to augment brain acetylcholine-mediated neurotransmission.

The therapeutic efficacy is measured by the degree to which cognitive and other neurobehavioral disabilities associated with dementias of the Alzheimer type, as documented by the use of standard scales, are reduced.

The following examples illustrate the invention.

EXAMPLE 1

Orally Disintegrating Tablets Containing 15 mg of Donepezil Hydrochloride and 4 mg of Ondansetron.

One and a half kilogram of donepezil hydrochloride and 1.8 kg of corn starch are mixed thoroughly until complete homogenizing of the mixture which, after a passage through a 35 mesh sieve, is added with a previously prepared mixture of 400 g of ondansetron base, thoroughly stirred together with 2.4 kg of corn starch and sieved at 35 mesh. The mixture thus obtained is added with 0.6 kg of strawberry flavor powder, 0.2 kg of sodium saccharin, 13.08 kg of lactose, 4.4 kg of microcrystalline cellulose, and 2.9 kg of sorbitol. The mixture is mixed until complete homogenization, then it is added with 0.1 kg of magnesium stearate, mixed again and compressed with punches of 7 mm to obtain 100,000 orally disintegrating tablets having the following composition

| | |
|---|---|
| Donepezil hydrochloride | 15.00 mg |
| Ondansetron | 4.00 mg |
| Corn starch | 42.00 mg |
| Strawberry flavor powder | 6.00 mg |
| Sodium saccharin | 2.00 mg |
| Lactose | 130.00 mg |
| Microcrystalline cellulose | 44.00 mg |
| Sorbitol | 29.00 mg |
| Magnesium stearate | 1.00 mg |

EXAMPLE 2

Capsules for IR oral administration are prepared by mixing the following ingredients:

| Ingredients | Parts by weight |
|---|---|
| Rivastigmine (as hydrogen tartrate) | 900 |
| Domperidone (as maleate) | 1,000 |
| Lactose USP | 7,350 |
| Colloidal silicon dioxide | 50 |

After mixing, the mixture is screened through a 40 mesh screen and introduced in two-piece hard gelatin capsules No. 3, each containing 9 mg of rivastigmine and 10 mg of domperidone.

EXAMPLE 3

Tablets for IR oral administration containing 5 mg of donepezil hydrochloride formulated with a pharmaceutical carrier, tablets containing 10 mg of donepezil hydrochloride formulated with a pharmaceutical carrier and tablets containing 10 mg of metoclopramide formulated with a pharmaceutical carrier are distributed in capsules as described in GB 1,254,580, such that unit dosage forms containing 15 mg of donepezil hydrochloride and 10 mg of metoclopramide are prepared.

EXAMPLE 4

The calculated amounts of metoclopramimide monohydrochloride monohydrate, galantamine hydrobromide, methyl parahydroxybenzoate, propyl parahydroxybenzoate, sodium saccharin, sodium sorbate, hydroxymethylcellulose, propylene glycol, ethanol, mandarin oil, caramel oil, custard oil, sodium hydroxide and purified water are mixed and formulated, according to conventional techniques, to prepare 100 ml of an oral solution, containing 10 mg/ml of metoclopramide and 6 mg/ml of galantamine, for a IR administration, having the following composition

| | |
|---|---|
| metoclopramide monohydrochloride monohydrate | 105.000 mg |
| galantamine hydrobromide | 7.668 mg |
| methyl p-hydroxybenzoate | 80.000 mg |
| propyl p-hydroxybenzoate | 20.000 mg |
| sodium sorbate | 100.000 mg |
| hydroxymethylcellulose | 400.000 mg |
| sodium saccharin | 0.076 mg |
| propylene glycol | 0.500 ml |

| | |
|---|---|
| ethanol | 1.000 ml |
| mandarin oil | 0.400 ml |
| caramel oil | 0.500 ml |
| custard oil | 0.010 ml |
| sodium hydroxide | to pH 3.0 |
| purified water | to 100.000 ml |

EXAMPLE 5

The calculated amounts of galantamine hydrobromide, metoclopramimide monohydrochloride monohydrate, guar gum, methyl cellulose, ethyl cellulose, silica gel, potato starch, sorbitol and pentaerytritol are mixed and formulated, according to conventional techniques, to prepare 150-mg IR-tablets having the following composition

| | |
|---|---|
| Galantamine hydrobromide | 23.06 mg |
| Metoclopramide monohydrochloride monohydrate | 10.50 mg |
| Guar gum | 2.00 mg |
| Methylcellulose | 2.00 mg |
| Ethylcellulose | 2.00 mg |
| Silica gel | 3.00 mg |
| Potato starch | 5.00 mg |
| Sorbitol | 2.44 mg |
| Pentaerythritol | 97.00 mg |

The invention claimed is:

1. A method for increasing the therapeutic effect of an acetyl choline esterase inhibitor (AChEI) in a patient suffering from an Alzheimer type dementia, which comprises administering to said patient from higher than 20 mg to 60 mg of donepezil and a pharmaceutically acceptable salt thereof, in combination with a non-anticholinergic antiemetic agent.

2. A method for increasing the therapeutic effect of an acetyl choline esterase inhibitor (AChEI) in a patient suffering from an Alzheimer type dementia, which comprises administering to said patient from 25 mg to 60 mg of donepezil and a pharmaceutically acceptable salt thereof, in combination with a non-anticholinergic antiemetic agent.

3. A method for increasing the therapeutic effect of an acetyl choline esterase inhibitor (AChEI) in a patient suffering from an Alzheimer type dementia, which comprises administering to said patient from 30 mg to 60 mg of donepezil and a pharmaceutically acceptable salt thereof, in combination with a non-anticholinergic antiemetic agent.

4. A method for increasing the therapeutic effect of an acetyl choline esterase inhibitor (AChEI) in a patient suffering from an Alzheimer type dementia, which comprises administering to said patient from 35 mg to 60 mg of donepezil and a pharmaceutically acceptable salt thereof, in combination with a non-anticholinergic antiemetic agent.

5. A method for increasing the therapeutic effect of an acetyl choline esterase inhibitor (AChEI) in a patient suffering from an Alzheimer type dementia, which comprises administering to said patient from 40 mg to 60 mg of donepezil and a pharmaceutically acceptable salt thereof, in combination with a non-anticholinergic antiemetic agent.

6. The method of any one of claim 1-5, wherein said non-anticholinergic antiemetic agent is selected from the group consisting of 5-HT3receptor antagonists, dopamine antagonists, H1 histamine receptor antagonists, NK1 receptor antagonists and cannabinoid agonists.

7. The method of claim 6, wherein said 5-HT3receptor antagonist is selected from the group consisting of ondansetron, granisetron, tropisetron, lerisetron, ramosetron, and pharmaceutically acceptable salts or solvates thereof.

8. The method of claim 6, wherein said dopamine antagonist is selected from the group consisting of domperidone, metoclopramide, bromopride, clebopride, alizapride, and pharmaceutically acceptable salts thereof.

9. The method of claim 6, wherein said HI histamine receptor antagonist is meclizine or a pharmaceutically acceptable salts or solvates thereof.

10. The method of claim 6, wherein said cannabinoid agonist is dronabinol or nabilone.

11. The method of claim 6, wherein said NK1receptor antagonist is aprepitant or casopitant.

12. The method of claim 6, wherein said non-anticholinergic antiemetic agent is a 5-HT3 receptor antagonist.

13. The method of any one of claim 1-5, wherein said non-anticholinergic antiemetic agent is administered at a dose from 50% to 300% of currently recommended dose for antiemetic therapy.

14. The method of claim 13, wherein the non-anticholinergic antiemetic agent and the AChEI are administered together or separately, in a unit form selected from the group consisting of a tablet, a capsule, a liquid solution, an oral suspension, and a transdermal patch.

15. The method of claim 13, wherein the non-anticholinergic antiemetic agent and the AChEI are both in immediate release (IR) or extended release (ER) form, or one of the non-anticholinergic antiemetic agent or the AChEI is in IR form and the other is in ER form.

16. The method of any one of claim 1-5, wherein the non-anticholinergic antiemetic agent and the donepezil are administered together or separately, in a unit form selected from the group consisting of a tablet, a capsule, a liquid solution, an oral suspension, and a transdermal patch.

17. The method of claim 16, wherein the non-anticholinergic antiemetic agent and the donepezil are both in immediate release (IR) or extended release (ER) form, or one of the non-anticholinergic antiemetic agent or the donepezil is in IR form and the other is in ER form.

18. A composition comprising a non-anticholinergic antiemetic agent and from 15 mg to 60 mg of donepezil and a pharmaceutically acceptable salt thereof.

19. A composition comprising a non-anticholinergic antiemetic agent and from 20 mg to 60 mg of donepezil and a pharmaceutically acceptable salt thereof.

20. A composition comprising a non-anticholinergic antiemetic agent and from 25 mg to 60 mg of donepezil and a pharmaceutically acceptable salt thereof.

21. A composition comprising a non-anticholinergic antiemetic agent and from 30 mg to 60 mg of donepezil and a pharmaceutically acceptable salt thereof.

22. A composition comprising a non-anticholinergic antiemetic agent and from 35 mg to 60 mg of donepezil and a pharmaceutically acceptable salt thereof.

23. A composition comprising a non-anticholinergic antiemetic agent and from 40 mg to 60 mg of donepezil and a pharmaceutically acceptable salt thereof.

* * * * *